(12) United States Patent
Castro

(10) Patent No.: US 10,383,637 B2
(45) Date of Patent: Aug. 20, 2019

(54) SNAP-ON SURGICAL CLIP CARTRIDGE

(71) Applicant: TELEFLEX MEDICAL INCORPORATED, Morrisville, NC (US)

(72) Inventor: Salvatore Castro, Raleigh, NC (US)

(73) Assignee: TELEFLEX MEDICAL INCORPORATED, Morrisville, NC (US)

(*) Notice: Subject to any disclaimer, the term of this patent is extended or adjusted under 35 U.S.C. 154(b) by 26 days.

(21) Appl. No.: 15/222,456

(22) Filed: Jul. 28, 2016

(65) Prior Publication Data

US 2017/0027576 A1 Feb. 2, 2017

Related U.S. Application Data

(60) Provisional application No. 62/199,142, filed on Jul. 30, 2015.

(51) Int. Cl.
| | |
|---|---|
| *A61B 17/10* | (2006.01) |
| *A61B 17/08* | (2006.01) |
| *A61B 17/068* | (2006.01) |
| *A61B 17/128* | (2006.01) |
| *A61B 17/122* | (2006.01) |
| *A61B 17/00* | (2006.01) |
| *A61B 17/12* | (2006.01) |
| *A61B 90/30* | (2016.01) |

(52) U.S. Cl.
CPC ...... *A61B 17/1285* (2013.01); *A61B 17/1222* (2013.01); *A61B 17/122* (2013.01); *A61B 2017/00362* (2013.01); *A61B 2017/12004* (2013.01); *A61B 2090/309* (2016.02)

(58) Field of Classification Search
CPC ............ A61B 17/1285; A61B 17/1222; A61B 2017/00362; A61B 2017/00296
See application file for complete search history.

(56) References Cited

U.S. PATENT DOCUMENTS

| | | |
|---|---|---|
| 3,270,745 A | 9/1966 | Charle |
| 3,326,216 A | 6/1967 | Wood |
| 3,363,628 A | 1/1968 | Wood |
| 3,439,522 A | 4/1969 | Wood |
| 3,439,523 A | 4/1969 | Wood |
| 3,713,533 A | 1/1973 | Reimels |
| 4,076,120 A | 2/1978 | Carroll et al. |

(Continued)

*Primary Examiner* — Tuan V Nguyen
(74) *Attorney, Agent, or Firm* — Baker & Hostetler LLP

(57) ABSTRACT

A surgical clip cartridge, assembly, and method are provided for the storage, delivery, and loading of clips, such as those used in a surgical ligating process. The surgical clip cartridge includes a base portion extending in a longitudinal direction, the base portion having a bottom surface and defining a mounting groove for attaching the base portion onto a surgical instrument shaft. The base portion further includes a plurality of dividers extending from the base portion in a direction opposite of the bottom surface, and the plurality of dividers may be used to retain individual surgical clips therebetween for subsequent retrieval and loading onto a clip applier. The attachment of the surgical clip cartridge to the surgical instrument shaft enables the surgical clip cartridge to be deployed intracorporeally for use in surgical operations requiring applications of multiple surgical clips.

18 Claims, 30 Drawing Sheets

(56) References Cited

U.S. PATENT DOCUMENTS

| | | | |
|---|---|---|---|
| 4,146,130 A | | 3/1979 | Samuels et al. |
| 4,509,518 A | | 4/1985 | McGarry et al. |
| 4,696,396 A | | 9/1987 | Samuels et al. |
| 4,936,447 A | * | 6/1990 | Peiffer ................ A61B 17/1222 206/339 |
| 4,972,949 A | * | 11/1990 | Peiffer ................ A61B 17/1222 206/339 |
| 5,046,611 A | | 9/1991 | Oh |
| 5,201,416 A | | 4/1993 | Taylor |
| 5,509,920 A | | 4/1996 | Phillips et al. |
| 5,564,262 A | | 10/1996 | Bevis et al. |
| 6,863,672 B2 | | 3/2005 | Reiley et al. |
| 7,125,403 B2 | * | 10/2006 | Julian ............... A61B 17/00234 606/1 |
| 2002/0017472 A1 | * | 2/2002 | Weisshaupt ........ A61B 17/1222 206/339 |
| 2002/0120254 A1 | * | 8/2002 | Julian ............... A61B 17/00234 606/1 |
| 2004/0059359 A1 | | 3/2004 | Wilson, Jr. |
| 2005/0234297 A1 | * | 10/2005 | Devierre ............ A61B 1/00087 600/153 |
| 2006/0124485 A1 | | 6/2006 | Kennedy |
| 2008/0277853 A1 | | 11/2008 | Menn |
| 2009/0236399 A1 | * | 9/2009 | Bilotti .................. A61B 1/0014 227/180.1 |
| 2010/0048988 A1 | * | 2/2010 | Pastorelli ........... A61B 1/00087 600/104 |
| 2013/0206160 A1 | * | 8/2013 | Sanchez .................. A45D 2/48 132/218 |
| 2014/0296629 A1 | | 10/2014 | Chang et al. |

* cited by examiner

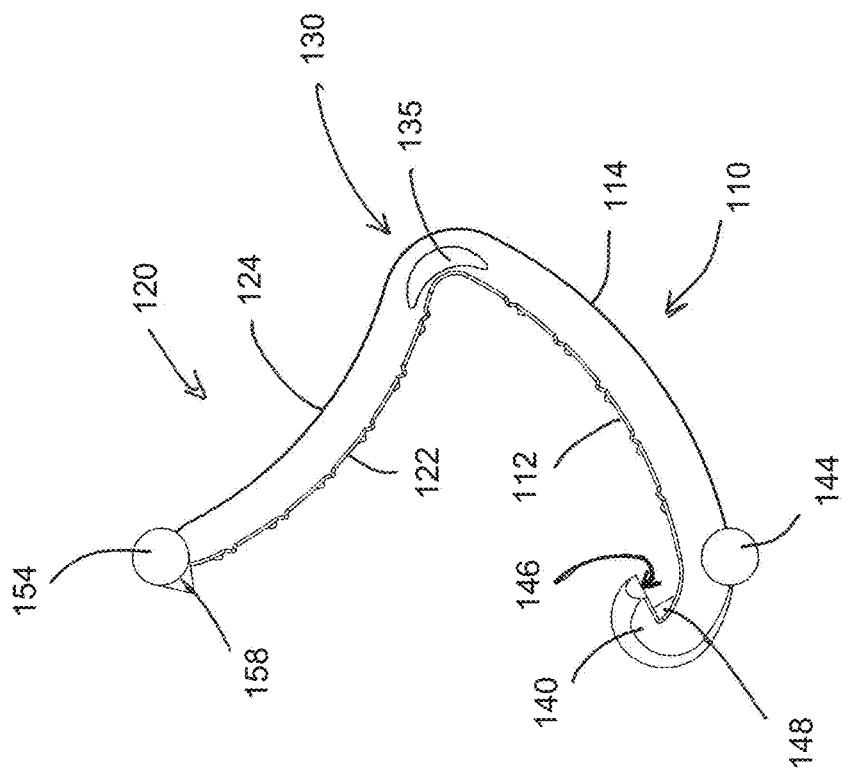

SNAP-ON SURGICAL CLIP CARTRIDGE

CROSS-REFERENCE TO RELATED APPLICATION

This patent application claims the priority benefit of U.S. Provisional Patent Application No. 62/199,142, filed Jul. 30, 2015, which is incorporated herein in its entirety by this reference.

TECHNICAL FIELD

The present disclosure relates to storage, delivery, and loading of clips, such as surgical ligating clips for use in surgical procedures. In particular, the present disclosure relates to a snap-on surgical clip cartridge configured to retain and dispense clips intracorporeally during a surgical operation.

DESCRIPTION OF RELATED ART

Many surgical procedures require vessels or other tissues of the human body to be ligated during the surgical process. For example, many surgical procedures require cutting blood vessels (e.g., veins or arteries), and these blood vessels may require ligation to stop or reduce bleeding. In some instances, a surgeon may wish to ligate the vessel temporarily to reduce blood flow to the surgical site during the surgical procedure. In other instances, a surgeon may wish to permanently ligate a vessel. Ligation of vessels or other tissues can be performed by closing the vessel with a ligating clip, or by suturing the vessel with surgical thread. The use of surgical thread for ligation requires complex manipulations of the needle and suture material to form the knots required to secure the vessel. Such complex manipulations are time-consuming and difficult to perform, particularly in endoscopic surgical procedures, which are characterized by limited space and visibility. By contrast, ligating clips are relatively easy and quick to apply. Accordingly, the use of ligating clips in endoscopic as well as open surgical procedures has grown dramatically.

Various types of hemostatic and aneurysm clips are used in surgery for ligating blood vessels or other tissues to stop the flow of blood. Such clips have also been used for interrupting or occluding ducts and vessels in particular surgeries, such as sterilization procedures. Typically, a clip is applied to the vessel or other tissue by using a dedicated mechanical instrument commonly referred to as a surgical clip applier, ligating clip applier, or hemostatic clip applier. The clip is permanently left in place after application to the tissue.

Ligating clips can be classified according to their geometric configuration (e.g., symmetric clips or asymmetric clips), and according to the material from which they are manufactured (e.g., metal clips or polymeric clips). Symmetric clips are generally "C", "U", or "V" shaped and thus are substantially symmetrical about a central, longitudinal axis extending between the legs of the clip. Symmetric clips are usually constructed from metals such as stainless steel, titanium, tantalum, or alloys thereof. An example of one such clip is disclosed in U.S. Pat. No. 5,509,920 to Phillips et al. By means of a dedicated clip applier, the metal clip is permanently deformed over the vessel. Asymmetric clips are usually constructed of polymeric material.

Because clips of the type just described are small and several clips are often used in a surgical procedure, clip holding devices are employed to store and retain multiple clips between the time of their manufacture and/or packaging and ultimate use in a surgical procedure. Numerous surgical clip cartridges have been developed, some of which strive to prevent the clips from becoming unduly loosened or even completely dislodged during shipment and handling. Surgical clip cartridges are intended for use with "manual" clip appliers.

As used herein, the term "automatic" denotes the kind of clip appliers that retain a plurality of hemostatic clips adjacent to the jaws of a clip applier in a way such that a new clip is automatically fed to the jaws after the previous clip has been crimped into place. An example of an applier that dispenses a plurality of clips for sequential application is disclosed in U.S. Pat. No. 4,509,518 to McGarry et al.

By contrast, the term "manual" denotes the kind of clip appliers that receive one clip at a time between the jaws, and which have to be reloaded manually after the previous clip has been crimped. These manual instruments usually have a forceps-type design and the reloading operation is generally accomplished by inserting the jaws of the applier into a clip holder or cartridge and engaging or grasping a clip contained therein. The jaws of the clip applier generally have longitudinal grooves to receive the clip legs and can have end-dams at the distal end of each groove to limit distal movement of the clip. The clip is secured in the jaws by the natural resiliency of the clip legs and by the end-dams if they are present. An example of a forceps-type applier having conformal jaws used to grip and maintain alignment of the clip during deformation is disclosed in U.S. Pat. No. 3,326,216 to Wood.

Many types of surgical clip cartridges currently available contain a plurality of longitudinally spaced clip retaining chambers. A single clip is retained in each chamber by a variety of means, and is removed from its chamber by a forceps-type clip applier that is inserted into the selected clip chamber and secured to the clip sufficiently to overcome whatever clip retention means is utilized, thereby enabling the clip to be removed from the clip chamber.

Various mechanisms are known by which clips can be retained within the chambers of surgical clip cartridges. In all instances, a desirable goal of such cartridges is to minimize the forces required to load the clip into the applier and to then remove it from the cartridge while maximizing the security with which the clip is held in the cartridge and, subsequently, the applier jaws prior to use. With respect to metallic clips, friction between the clip and the side walls of its individual chamber is often sufficient to retain the clip. The surgical clip cartridges are generally made of molded plastic material, such that the walls of each clip chamber are somewhat resilient and able to be pushed away from each other when the clip applier jaws are inserted into the chamber to retrieve the clip. An example of a cartridge holding the clips in their respective clip chambers by means of frictional engagement with the side walls of each chamber is shown in U.S. Pat. No. 4,076,120 to Carroll et al. Another example of a cartridge holding the clips in their respective clip chambers is shown in U.S. Pat. No. 6,863,672 to Wilson, Jr.

In some surgical clip cartridges designed for metallic clips, each individual clip chamber is provided with a central post generally conforming to the shape of the open clip although being slightly larger so that when the clip is pushed onto the central post, frictional contact between the legs of the clip and the central post retains the clip within its chamber. Cartridges of this type are shown in U.S. Pat. Nos. 3,270,745; 3,326,216; 3,363,628; 3,439,522; and 3,439,523, all issued to Wood.

Cartridges in the related art are also known that retain clips in a partially straightened state by maintaining each clip under tension within its chamber, through the interaction between the central post in the chamber and the central part of the clip and protrusions extending into each chamber toward the central post (from the ends). The clip is retained by having its central hinge part pushed upwardly by the central post and its ends pushed downwardly by the protrusions. Such a cartridge is shown in U.S. Pat. No. 3,713,533 to Reimels and U.S. Pat. No. 4,146,130 to Samuels et al.

U.S. Pat. No. 4,696,396 to Samuels discloses another type of cartridge that has a plurality of ribs extending from each side wall of each clip chamber inwardly toward the clip to retain the clip by frictional engagement with the ribs. The aforementioned U.S. Pat. No. 4,146,130 to Samuels et al. shows an alternative embodiment for the situation where clips are intended to be loosely maintained in the cartridge without frictional engagement between the clips and the chamber, the clips in such an event being retained in each cartridge by a covering tape which can be easily severed by the applier as desired.

While the above cartridges for metal and polymeric clips have been used with adequate results, there are several disadvantages to the composition and structural design of the cartridges that limits their functionality during use.

First, the cartridges in the related art are typically hand-held by an operator or placed on a surface, such as a table or a tray, while the surgical clips are loaded from the clip cartridge and loaded onto a clip applier. The result is that the cartridges in the related art may be prone to being dropped, misplaced, or contaminated during a surgical procedure. Second, the cartridges in the related art are used to supply clips to a clip applier extracorporeally. In other words, the cartridges are maintained outside the patient and away from the operation area. In manual ligation, a clip cartridge containing clips is set within the operating field. The surgeon is restricted to loading a clip from the clip cartridge onto the clip applier outside the patient. Once the clip has been loaded from the cartridge onto the clip applier, the clip applier together with the clip is inserted into the patient to achieve ligation. However, this method requires the surgeon to move back and forth from the operative site to the clip cartridge outside of the patient for reloading, resulting in time loss and direct visualization loss.

As such, the present disclosure contemplates an improved surgical clip cartridge that allows quicker clip loading with no visualization loss.

SUMMARY

According to one aspect of the present disclosure, a surgical clip cartridge includes a base portion extending in a longitudinal direction, and the base portion has a bottom surface. The surgical clip cartridge further includes a plurality of dividers extending from the base portion in a direction opposite of the bottom surface, and the base portion defines a mounting groove for attaching the base portion onto a surgical instrument shaft.

In one aspect, the mounting groove extends in a direction parallel to the longitudinal direction of the base portion. In one aspect, the mounting groove includes at least one docking portion, and the docking portion defines at least one concave semi-circular surface that is configured to conform around the surgical instrument shaft. The concave semi-circular surface has a first radius, and the first radius is less than or equal to an outer radius of the surgical instrument shaft to provide an annular fit when the docking portion is attached to the surgical instrument shaft. The concave semi-circular surface revolves about a central longitudinal axis of the docking portion, and the revolution of the concave semi-circular surface is greater than or equal to 180°. In one aspect, a surface of the at least one docking portion includes one or more of a friction material, knurling, notches, and protrusions to prevent axial and/or rotational displacement when the docking portion is attached to the surgical instrument shaft.

In one aspect, the mounting groove defines at least two docking portions, a first docking portion of the at least two docking portions being located on a proximal end of the base portion in the longitudinal direction, and the second docking portion of the at least two docking portions being located on a distal end of the base portion in the longitudinal direction. In one aspect, the at least one docking portion extends continuously from a proximal end to a distal end of the base portion.

In one aspect, at least one divider of the plurality of dividers includes at least one wall surface extending away from the base portion in a vertical direction perpendicular to the longitudinal direction. In one aspect, the at least one wall surface is a planar wall surface. In one aspect, the at least one divider includes an upper surface, and the upper surface includes at least a horizontally extending segment and a sloped segment extending upwardly towards the horizontally extending segment and towards a center of the at least one divider. In one aspect, an upper portion of the at least one wall surface includes a latching protrusion, the latching protrusion extending at least in the longitudinal direction. In one aspect, the latching protrusion is for interfacing with at least one portion of a surgical clip, the at least one portion being one of a surface, a depression, and an orifice of the surgical clip. In one aspect, the latching protrusion is configured to prevent movement of a surgical clip in directions perpendicular to the longitudinal direction of the base portion.

In one aspect, the surgical clip cartridge further comprises a plurality of spacer portions extending from the base portion in a direction opposite of the bottom surface, and a spacer portion of the plurality of spacer portions is disposed between pairs of facing dividers of the plurality of dividers. In one aspect, the spacer portion defines a top surface, the top surface having a concave segment and a convex segment. In one aspect, the spacer portion defines at least one inwardly tapering section and a depth of the inwardly tapering section increases moving from an upper portion of the spacer towards a lower portion of the spacer.

According to one aspect, a surgical device for storage, delivery, and loading of surgical clips to a clip applier includes a surgical instrument with an elongated shaft extending along a first longitudinal axis. The surgical device further includes a surgical clip cartridge including a base portion extending along a second longitudinal direction. The base portion has a bottom surface and defines a mounting groove to secure the surgical clip cartridge onto at least a portion of the elongated shaft of the surgical instrument.

In one aspect, the mounting groove includes at least one docking portion, and the docking portion defines a concave semi-circular surface configured to conform around the elongated shaft. The concave semi-circular surface revolves about a central longitudinal axis of the docking portion, and the revolution of the concave semi-circular surface is greater than or equal to 180°. In one aspect, the surgical clip cartridge includes a plurality of dividers extending from the base portion in a direction opposite of the bottom surface, and pairs of facing dividers of the plurality of dividers are configured to receive and retain a surgical clip of the surgical clips therebetween.

BRIEF DESCRIPTION OF THE DRAWINGS

FIG. 3 shows a side view of the ligation clip of FIG. 12 in accordance with aspects of the disclosure.

DETAILED DESCRIPTION

Figure 1:
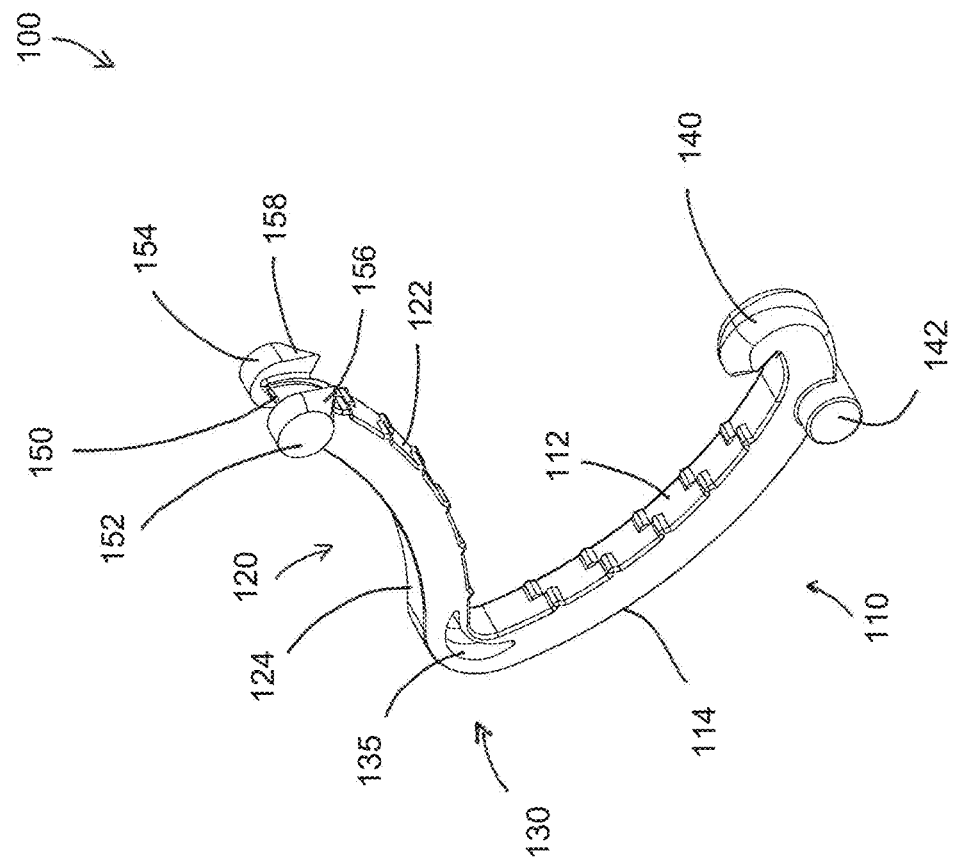
FIG. 1 shows a front perspective view of a ligation clip in accordance with aspects of the disclosure.

Now referring to the drawings, wherein like reference numerals refer to like elements, exemplary aspects of the present disclosure will now be discussed.

Figure 2:
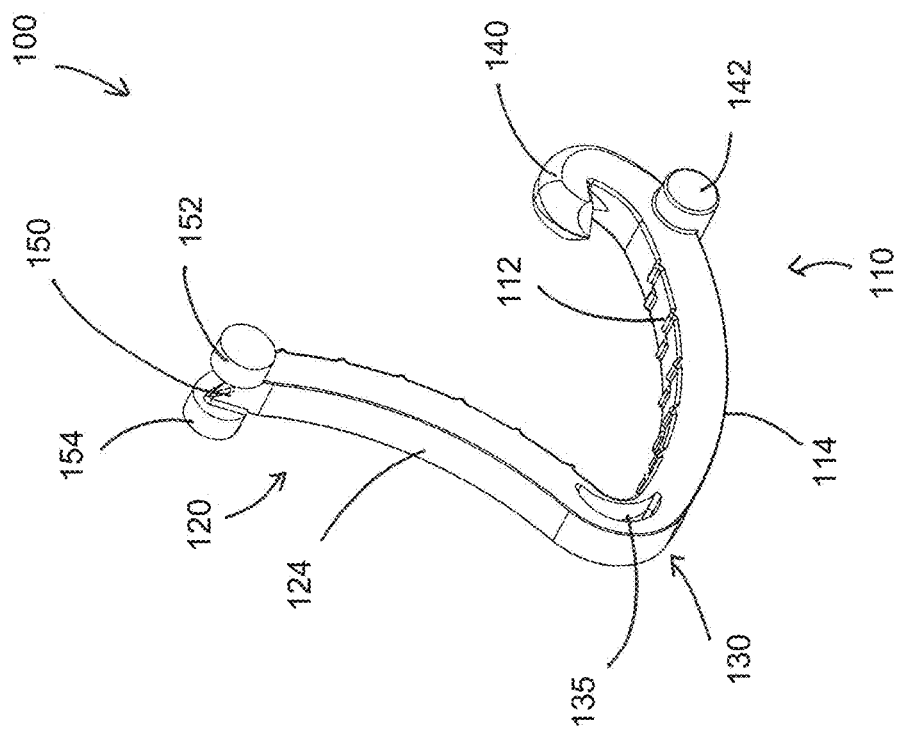
FIG. 2 shows a rear perspective view of the ligation clip of FIG. 12 in accordance with aspects of the disclosure.

FIGS. 1-3 shows an exemplary surgical clip 100 that may be used with the surgical clip cartridges of the present disclosure. The surgical clip 100 may be a hemostatic clip that is capable of being latched around a vessel or other type of tissue to ligate the vessel and thereby stop or reduce the flow of fluid through the vessel. The surgical clip 100 may be constructed from any suitable biocompatible material, such as metals and/or polymers.

In one aspect, the surgical clip 100 may comprise a first leg 110 and a second leg 120. The first leg 110 and the second leg 120 may be joined together at their proximal ends by an integral hinge section 130. The integral hinge section 130 may define a latching orifice 135, as will be described in further detail below.

The first leg 110 may define an inner concave surface 112 and an outer convex surface 114. The first leg 110 may transition to a curved, C-shaped hook section 140 at a distal end thereof. The C-shaped hook section 140 may define a beveled surface 146. An intersection between the beveled surface 146 and the first leg 110 may define a latching recess 148. A pair of bosses 142, 144 may extend laterally away from the first leg 110.

The second leg 120 may define an inner convex surface 122 and an outer concave surface 124. The second leg 120 may transition into a hook section 40 at a distal end thereof. The distal end of the second leg 120 may further define a tip section 150. A pair of bosses 152, 154 may extend laterally away from the second leg 120. The pair of bosses 152, 154 may each include at least one tissue penetrating teeth 156, 158, and the penetrating teeth 156, 158 may be oriented towards the first leg 110.

Figure 4B:
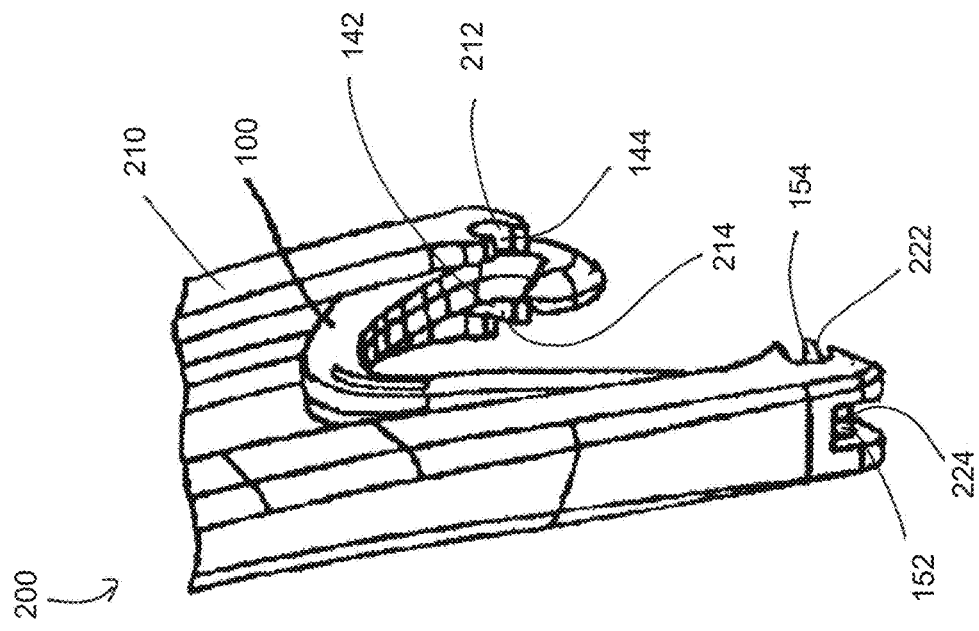
FIG. 4B shows a perspective view of the clip applier of FIG. 4A with a ligation clip loaded in accordance with aspects of the disclosure.
Figure 4A:
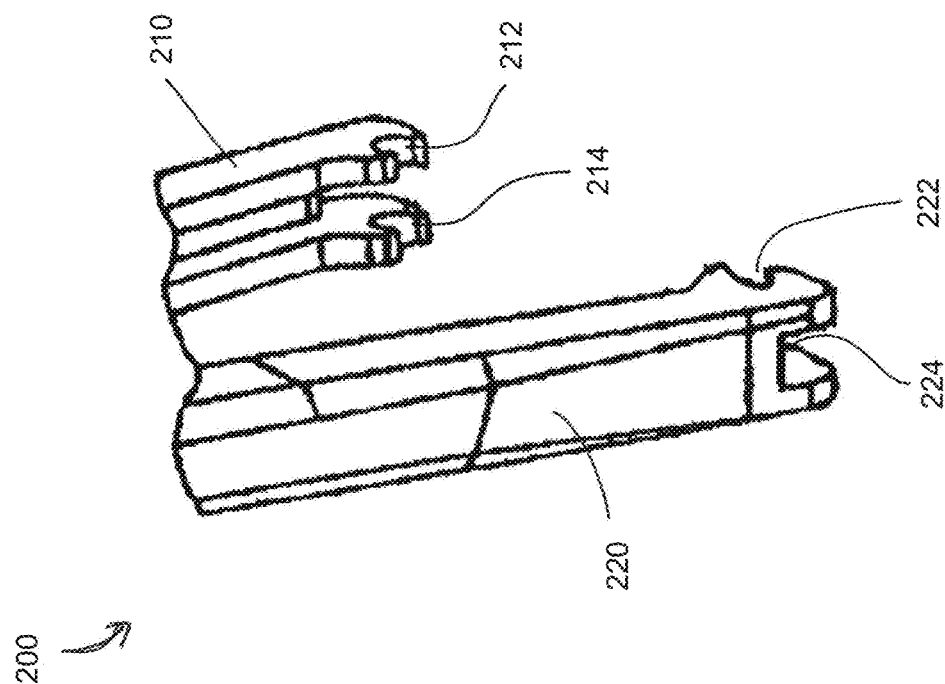
FIG. 4A shows a perspective view of a clip applier in accordance with aspects of the disclosure.

Turning to FIGS. 4A and 4B, an exemplary clip applier 200 is shown, and the clip applier 200 may be used to grasp and apply the surgical clip 100 onto a target vessel or other type of tissue. In one aspect, clip applier 200 may comprise a pair pivotable jaws 210, 220. The first jaw 210 of the pivotable jaws may include a pair of notches 212, 214. The second jaw 220 of the pivotable jaws may also include a pair of notches 222, 224. In one aspect, the clip applier 200 may be used to retrieve and load the surgical clip, for example, from a surgical clip cartridge.

The clip applier 200 may be positioned about the surgical clip 100. The notches 212, 214 of the first jaw 210 may be configured to receive and lock the bosses 142, 144 of the first leg 110, and the notches 222, 224 of the second jaw 220 may be configured to receive and lock the bosses 152, 154 of the second leg 120. Alternatively, the notches 212, 214 of the first jaw 210 may be configured to receive and lock the bosses 152, 154 of the second leg 120, and the notches 222, 224 of the second jaw 220 may be configured to receive and lock the bosses 142, 144 of the first leg 110. Once secured, a distal end of the clip applier 200, including the surgical clip 100, may be directed towards the target vessel or tissue. The first jaw 210 and the second jaw 220 may then be squeezed or forced closed towards each other. As this occurs, the first leg 110 and the second leg 120 of the surgical clip 100 may close upon the target vessel or tissue between the inner concave surface 112 and the inner convex surface 122. When sufficient force is applied via the clip applier 200, the tip section 150 may be forced past the beveled surface 146 and into the latching recess 148, thereby locking the two legs 110, 120 together. As discussed above, the surgical clip cartridges in the related art require that the surgeon move away from the operative site to retrieve additional clips, thereby resulting in time loss and direct visualization loss.

Figure 14:
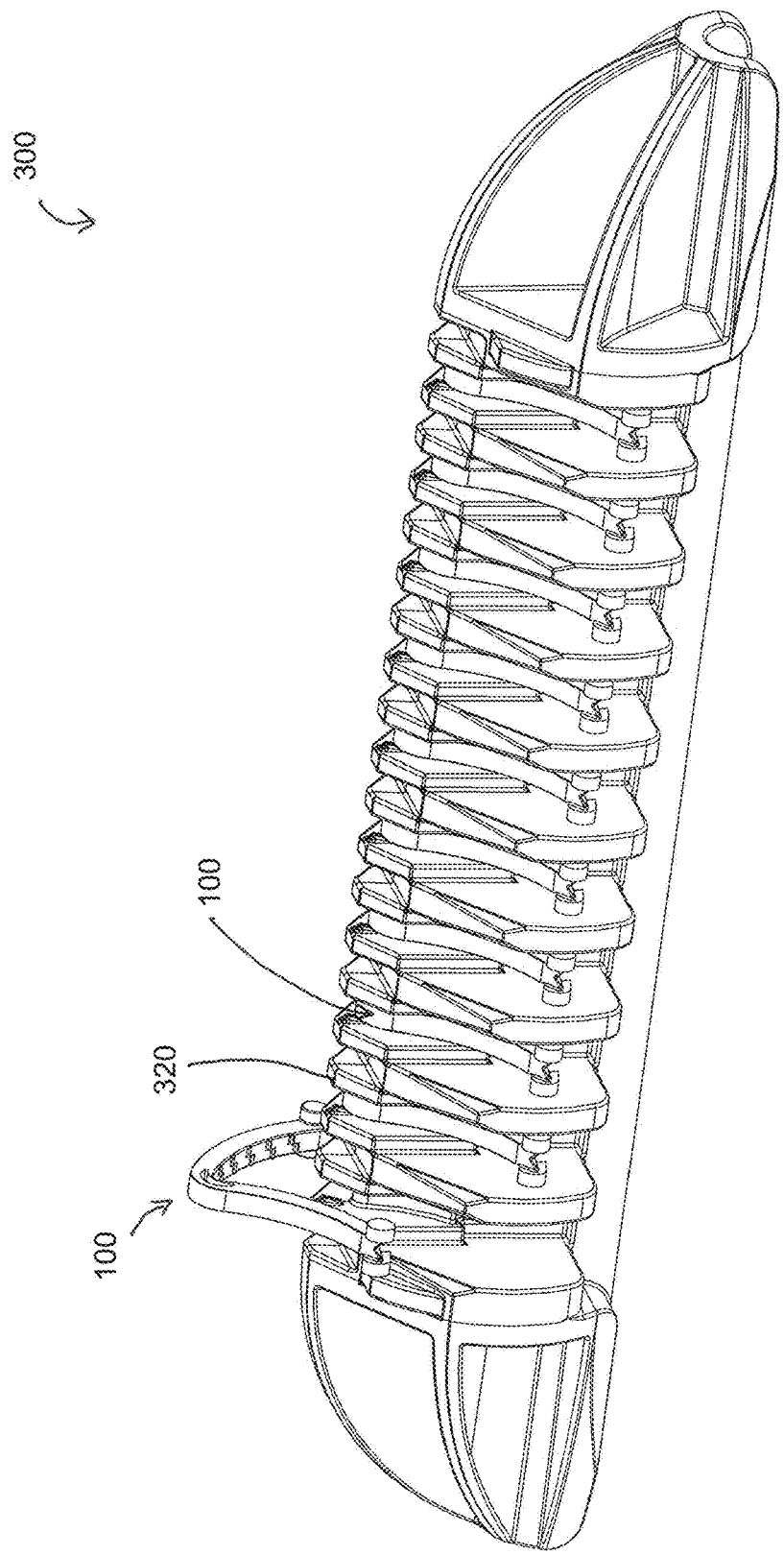
FIG. 14 shows a side perspective view of a snap-on surgical clip cartridge with clips loaded in accordance with aspects of the disclosure.
Figure 15:
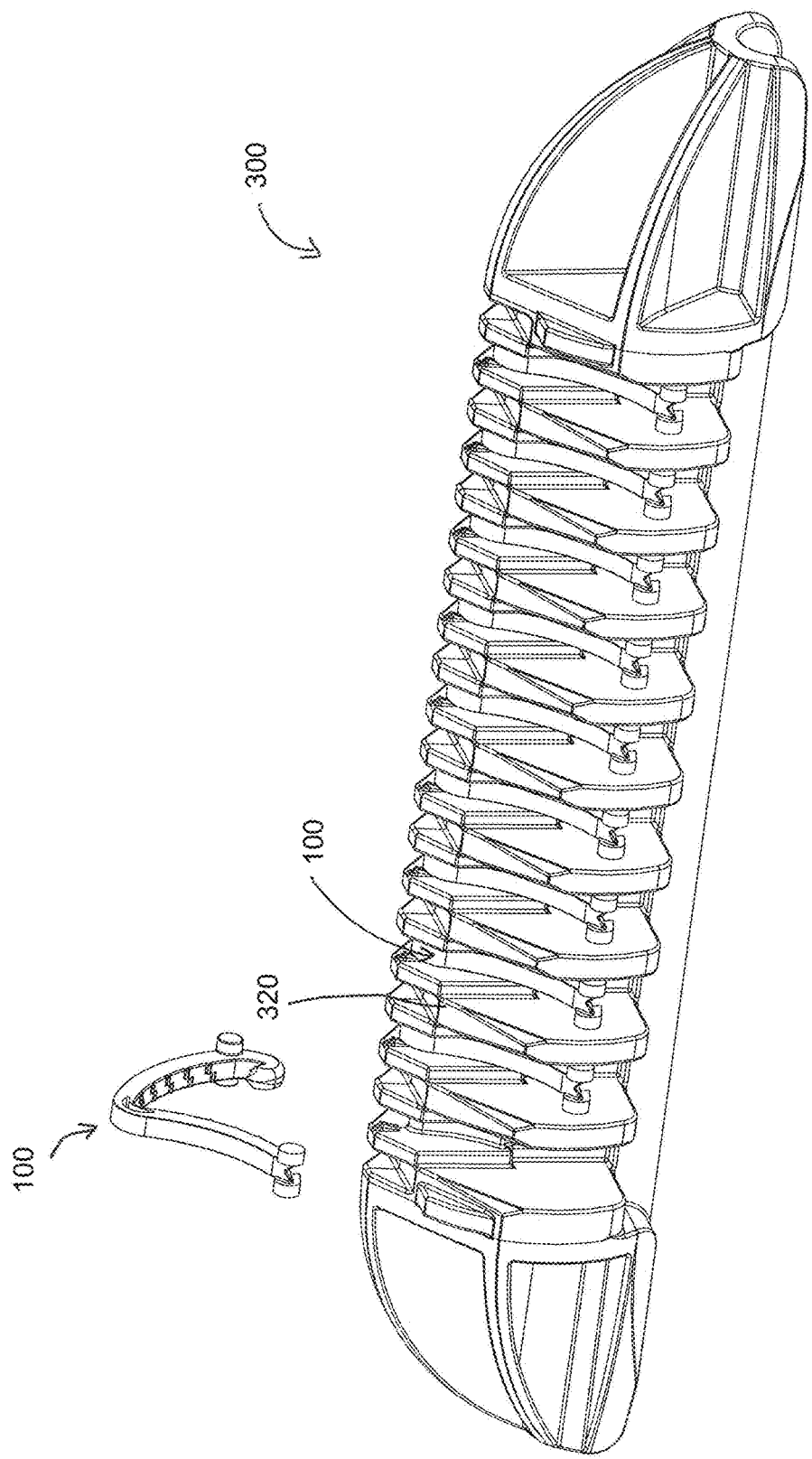
FIG. 15 shows a side perspective view of the snap-on surgical clip cartridge of FIG. 10, with a clip removed in accordance with aspects of the disclosure.
Figure 16:
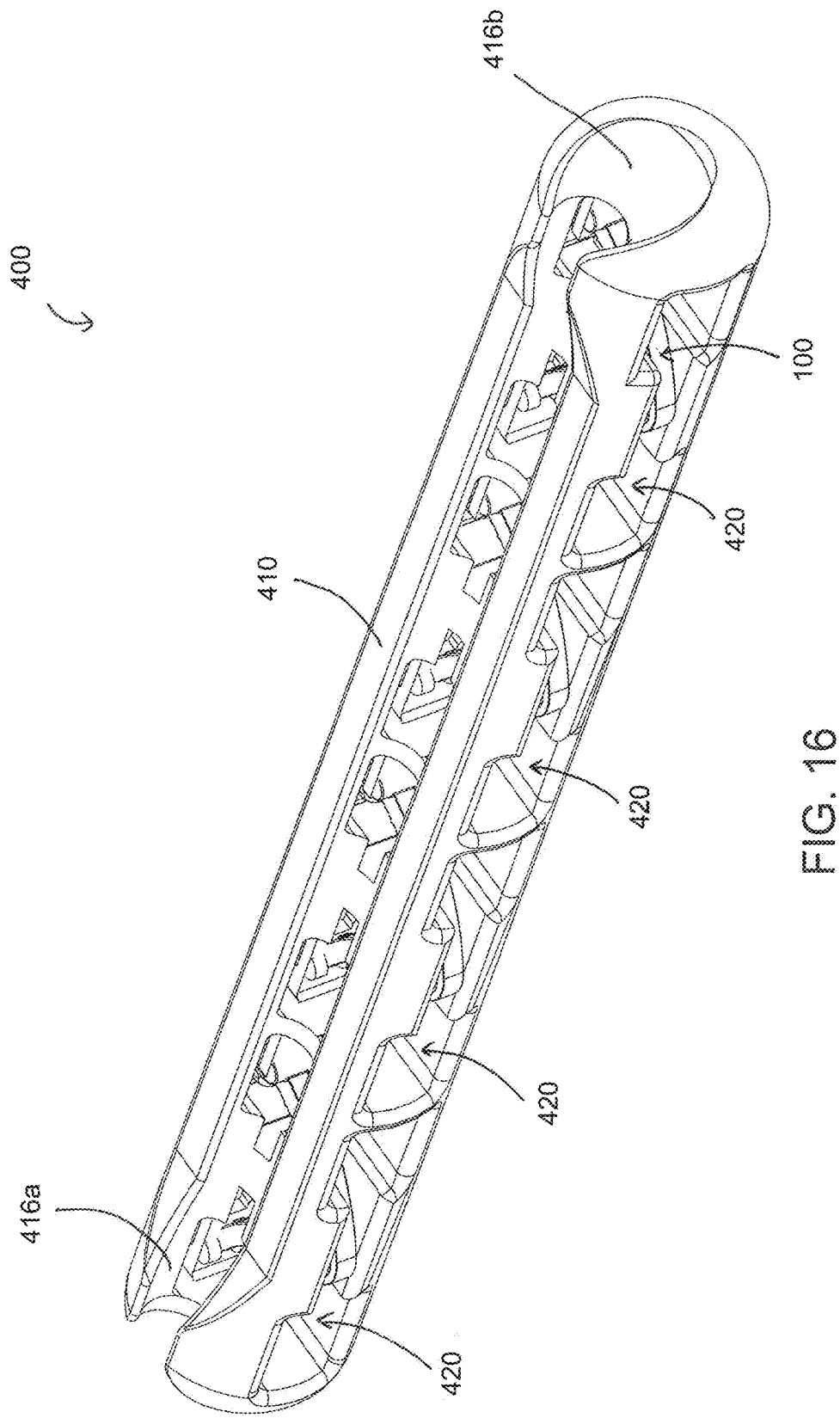
FIG. 16 shows a top perspective view of a snap-on surgical clip cartridge in accordance with aspects of the disclosure.
Figure 17:
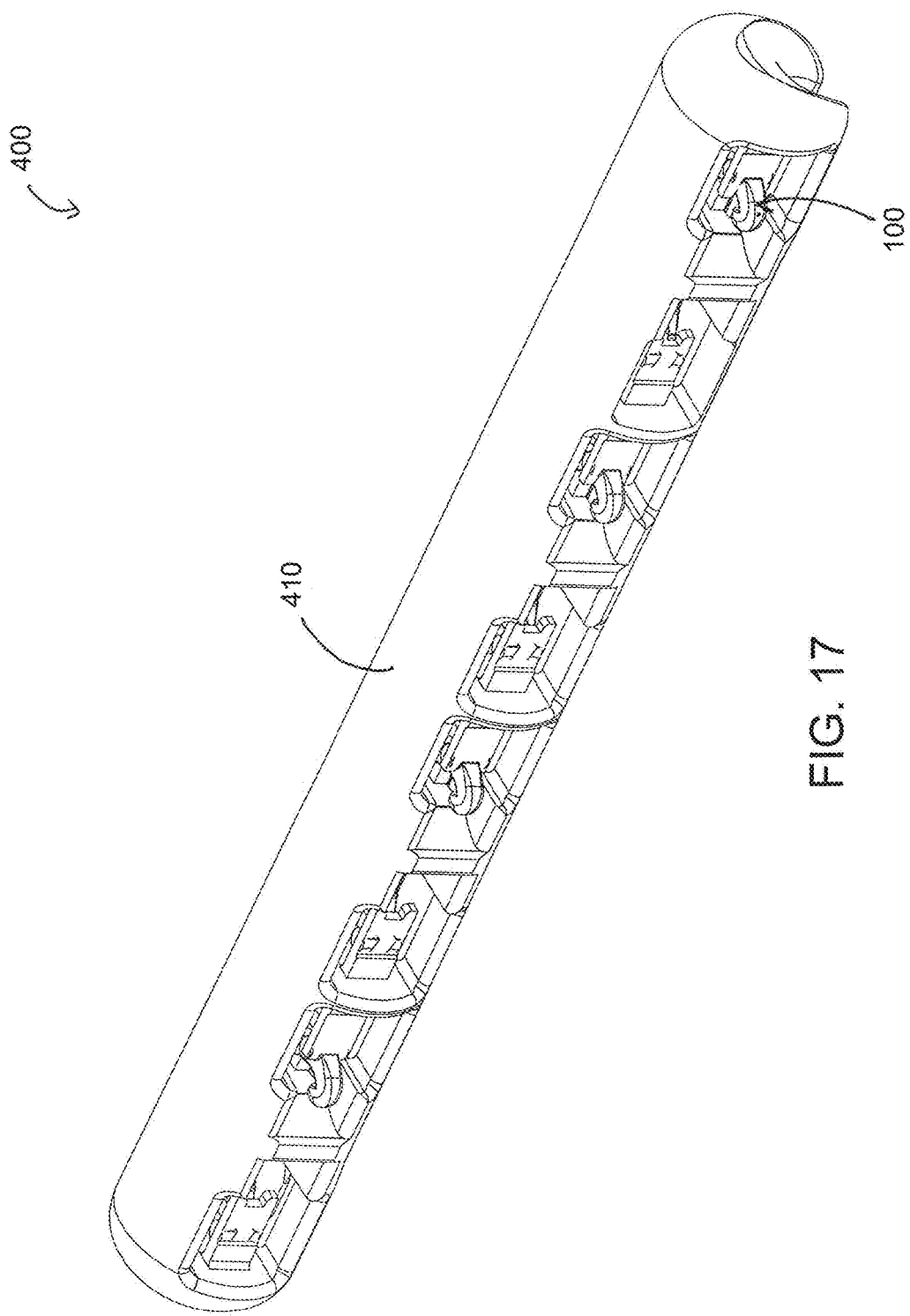
FIG. 17 shows a bottom perspective view of the snap-on surgical clip cartridge of FIG. 16 in accordance with aspects of the disclosure.

FIGS. 5-15 show views of a first exemplary surgical clip cartridge 300 in accordance with aspects of the present disclosure. FIGS. 16 and 17 further show the surgical clip cartridge 300 loaded with clips, such as the surgical clips 100 discussed above. Of course, other types of clips may be used with the surgical clip cartridge 300. In one aspect, the surgical clip cartridge 300 may include a base portion 310 extending in a longitudinal direction, and the base portion 310 may have at least a bottom surface 312. The surgical clip cartridge 300 may include a plurality of dividers 320 extending from the base portion 310 in a direction opposite of the bottom surface 312.

The base portion 310 may define a mounting groove 314 for attaching the base portion 310 onto a surgical instrument shaft, as will be described in further detail below with reference to FIG. 26. The mounting groove 314 may extend along the longitudinal direction. The mounting groove 314 may include at least one docking portion 316a, 316b, the at least one docking portion 316a, 316b may define a concave semi-circular surface configured to conform around the surgical instrument shaft. In one aspect, the concave semi-circular surface may have a first radius, and the first radius may be less than or equal to an outer radius of the surgical instrument shaft in order to provide an interference fit or an annular fit when the docking portion 316a, 316b is attached to the surgical instrument shaft. The interference or annular fit may utilize the flexibility the docking portion 316a, 316b to at least partially surround the surgical instrument shaft and maintain a snap-on attachment utilizing a hoop-strain attribute of the docking portion 316a, 316b.

The concave semi-circular surface may revolve about a central longitudinal axis of the docking portion 316a, 316b, and the revolution of the concave semi-circular surface may be greater than or equal to 180°. In one aspect, the angle of revolution is between about 180° to 270°. For example, the angle of revolution of the concave semi-circular surface may be between about 185° to 270°, or between about 220° to 245° to ensure a secure fit about the surgical instrument shaft, when attached, while enabling the surgical clip cartridge 300 to be snapped-on or snapped-off of the surgical instrument shaft using the force of a user's hands, for example. It will be appreciated by one skilled in the art, in view of the present disclosure, that the arc length and the revolution of the arc may be selected based on a size or radius of the surgical instrument shaft that the surgical clip cartridge 300 is intended to attach on to. Additionally or alternatively, the arc length and the revolution of the arc may be selected based on the material properties of the surgical clip cartridge 300, such as the resiliency, to ensure that the at least one docking portion 316a, 316b can be displaced sufficiently to engage and secure the surgical clip cartridge 300 onto the surgical instrument shaft without damage or failure during the product life.

In one aspect, the concave semi-circular surface of the at least one docking portion 316a, 316b may include one or more of a friction material, knurling, notches, and protrusions to prevent axial or rotational displacement when the docking portion 316a, 316b is attached to the surgical instrument shaft. The addition of one or more of the above surface features may prevent the base portion 310 from shifting relative to the surgical instrument shaft, thereby promoting accuracy and repeatability when a surgeon attempts to retrieve a clip 100 from the surgical clip cartridge 300 during a surgical procedure. In one aspect, the docking portion 316a, 316b and the surgical instrument shaft may include corresponding ribs and grooves to prevent axial and/or radial movement of the surgical clip cartridge 300 relative to the surgical instrument shaft once the surgical clip cartridge 300 has been mounted to the surgical instrument shaft.

Figure 6:
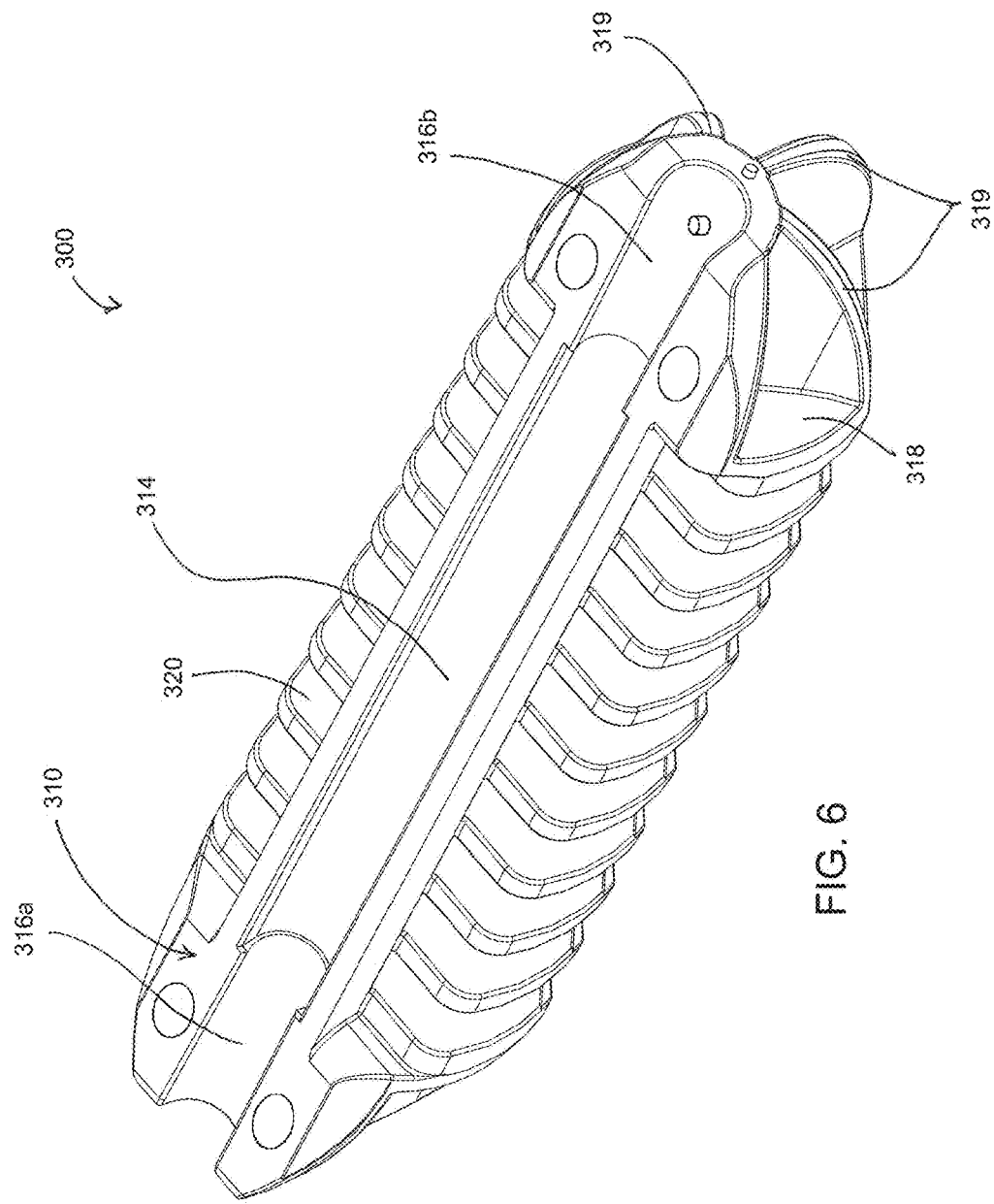
FIG. 6 shows a bottom perspective view of the snap-on surgical clip cartridge of FIG. 1 in accordance with aspects of the disclosure.
Figure 10:
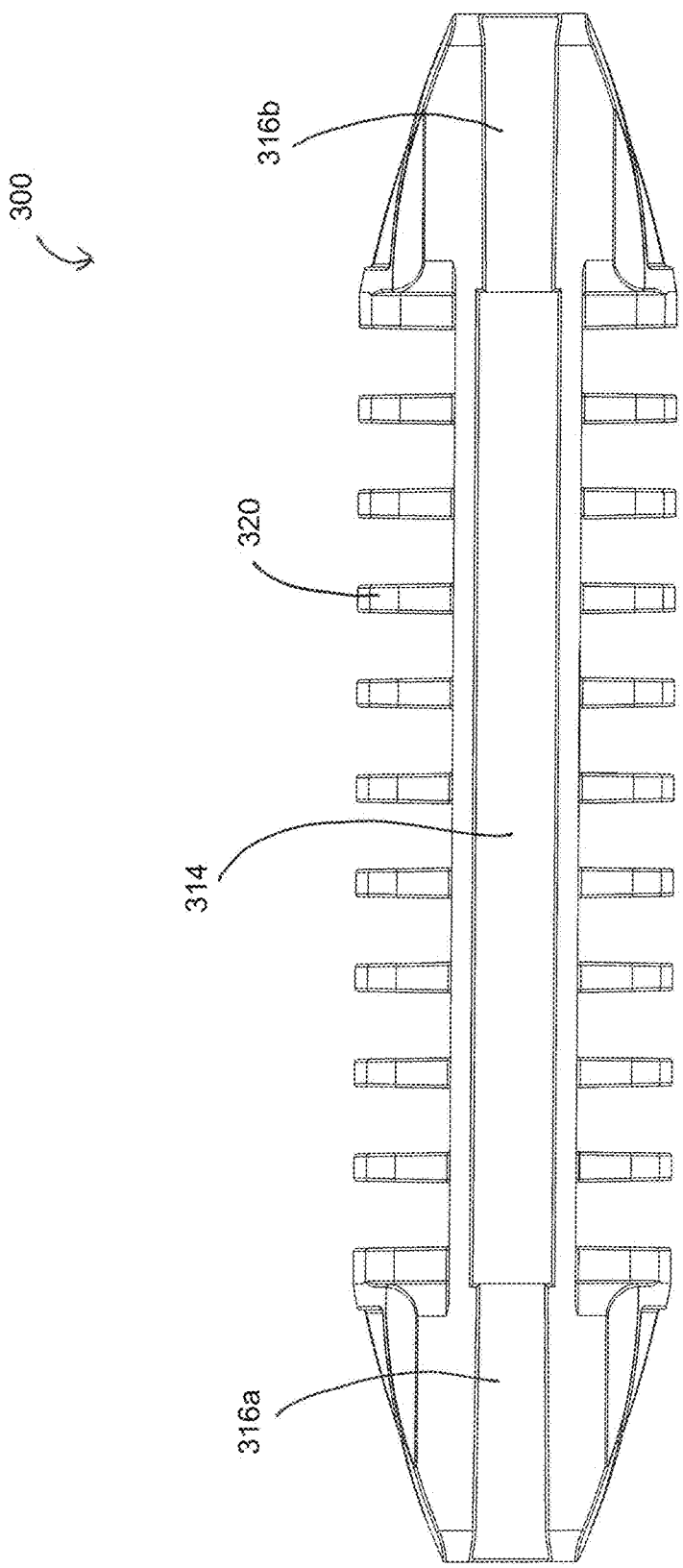
FIG. 10 shows a bottom view of the snap-on surgical clip cartridge of FIG. 1 in accordance with aspects of the disclosure.

In one aspect, as best shown in FIGS. 6 and 10, the mounting groove 314 may define at least two docking portions 316a, 316b, a first docking portion 316a of the at least two docking portions may be disposed on a proximal end of the base portion 310 in the longitudinal direction, and second docking portion 316b of the at least two docking portions being located on a distal end of the base portion 310 in the longitudinal direction. In one aspect, the at least one docking portion may extend continuously from a proximal end to a distal end of the base portion.

In one aspect, as best shown in FIGS. 5, 7, 9, 11, 12, and 13, the surgical clip cartridge 300 may include a plurality of dividers 320. Each of the plurality of dividers 320 may include at least one wall surface 322 extending away from the base portion 310 in a vertical direction perpendicular to the longitudinal direction. The at least one wall surface 322 may be a planar wall surface, although other surface contours promoting the insertion and removal of clips are of course contemplated. In one aspect, the at least one divider 320 may include an upper surface, and the upper surface may include a horizontally extending segment 324 and at least one sloped segment 326 extending upwardly towards the horizontally extending segment and towards a center of the at least one divider 320. In one aspect, the upper surface of the at least one divider 320 may generally define a trapezoidal shape. The trapezoidal shape of the at least one divider 320 may provide clearance and promote greater maneuverability of the surgical clip 100 once it has been disengaged from the surgical clip cartridge 300. For example, the sloped segments 326 may enable the C-shaped hook section 140 and/or the tip section 150 of the surgical clip 100 to clear the at least one divider 320 more quickly and allow the surgical clip 100 to be maneuvered along the longitudinal direction without interference with the surgical clip cartridge 300. The increased maneuverability may be particularly beneficial when the surgical clip cartridge 300 is used intracorporeally where there is a limited amount of space within the body cavity of a patient.

As shown in FIG. 14, the surgical clip 100 may be moved in the axial direction relative to the surgical clip cartridge 300 even though portions of the surgical clip 100 overlaps with an upper most portion of the surgical clip cartridge 300. Additionally, the sloped segment 326 may prevent the surgical clip 100 from snagging the surgical clip cartridge 300 in the event the surgical clip 100 is maneuvered laterally before the surgical clip 100 has completely cleared from the surgical clip cartridge 300. The sloped segment 326 may allow the C-shaped hook section 140 and/or the tip section 150 to ride along the sloped segment 326 to clear the surgical clip cartridge 300 without snagging during an operation.

In one aspect, an upper portion of the at least one wall surface 322 includes a latching protrusion 328. The latching protrusion 328 may extend from the at least one wall surface 322. The latching protrusion 328 may be used for interfacing with at least a portion of a surgical clip 100, such a surface, a depression, and/or an orifice of the surgical clip 100. In one aspect, the interfacing portion of the surgical clip 100 may be the latching orifice 135 disposed at the integral hinge section 130 of the surgical clip 100. In one aspect, the latching protrusion 328 may be configured to prevent movement of a surgical clip 100 in directions perpendicular to the longitudinal direction of the base portion 310. For example, the surgical clip 100 may be inserted into the surgical clip cartridge 300 such that the latching protrusion 328 is at least partially inserted into the latching orifice 135. In this arrangement, the latching orifice 135 and the latching protrusion 328 may be sized to limit or prevent any play or movement of the surgical clip 100 relative to the surgical clip cartridge 300. However, once a predetermined threshold force is applied to the surgical clip 100, via the clip applier 200 for example, the surgical clip 100 may be released from the latching protrusion 328.

Figure 9:
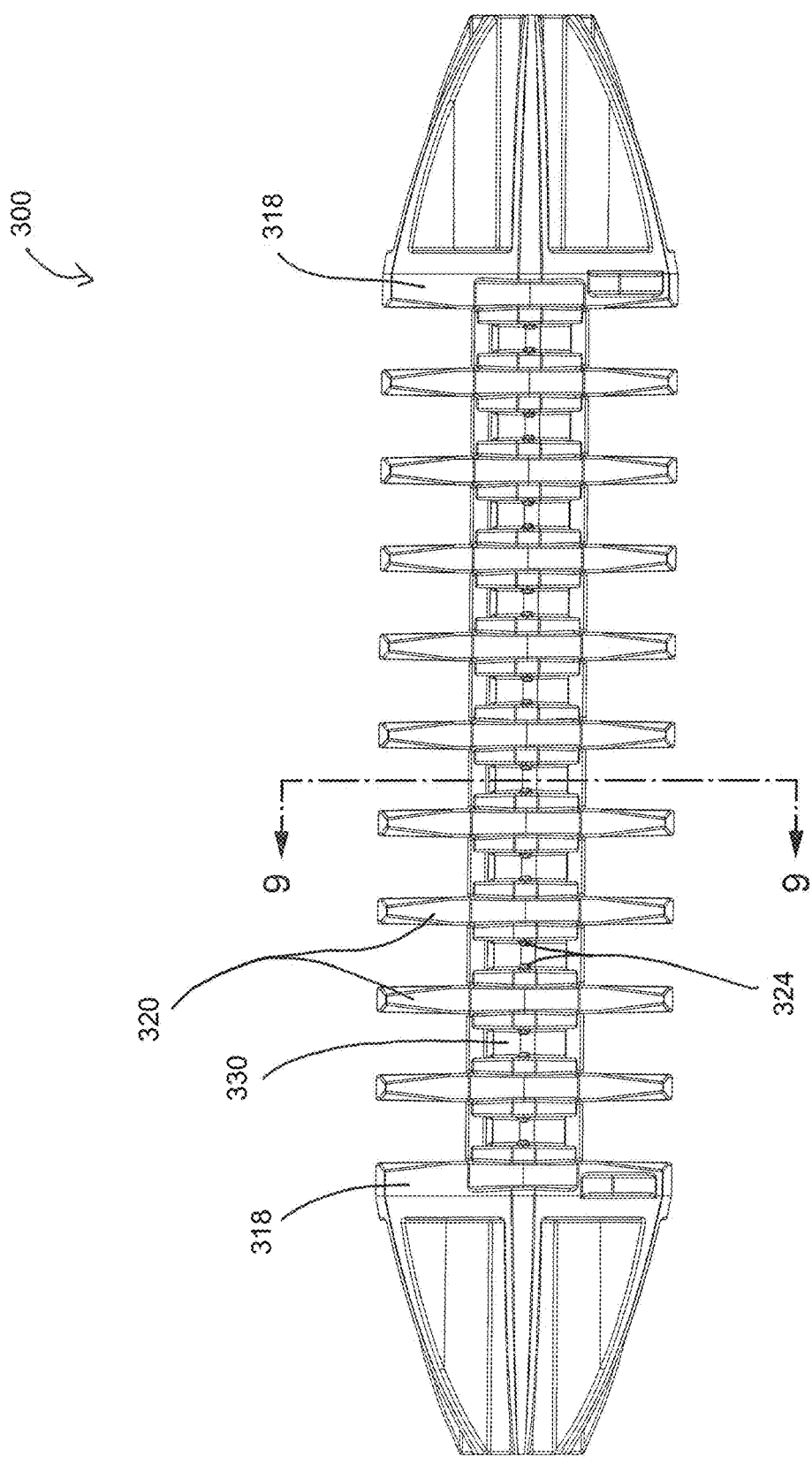
FIG. 9 shows a top view of the snap-on surgical clip cartridge of FIG. 1 in accordance with aspects of the disclosure.

As shown in FIGS. 7, 9, 11, 12, and 13, the surgical clip cartridge 300 may further comprise a plurality of spacer portions 330. The spacer portions 330 may extend from the base portion 310 in a direction opposite of the bottom surface 312. The spacer portion 330 of the plurality of spacer portions may be disposed between pairs of facing dividers 320 of the plurality of dividers. In one aspect, a width of the spacer portions 330 extending between a pair of dividers 320 may be at least a maximum width of the surgical clip 100. For example, the width of the spacer portions may be at least as wide as a lateral width of the pair of bosses 152, 154 of the surgical clip 100 (as shown in FIG. 1). In one aspect, as shown in FIG. 9, each pair of facing dividers 320 may include at least two latching protrusion 328 to interface with the latching orifice 135 of the surgical clip 100.

Figure 11:
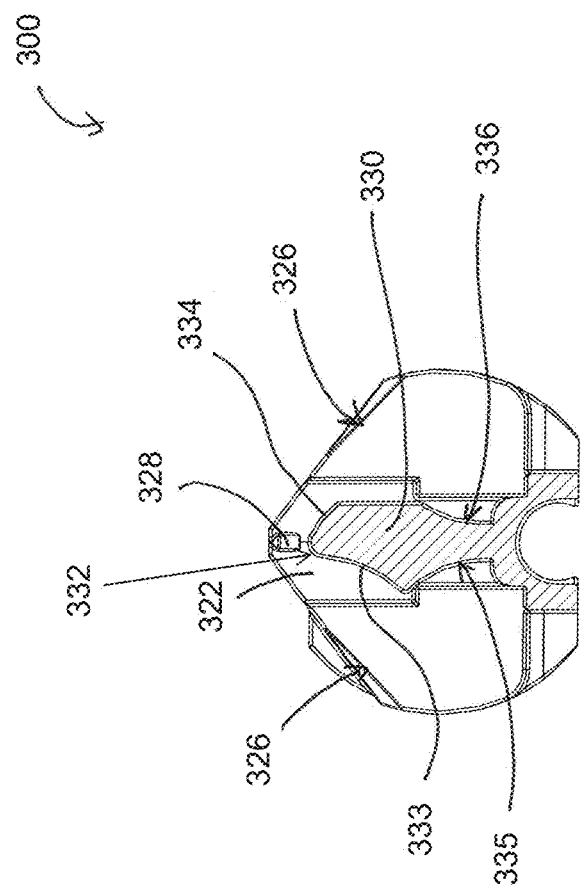
FIG. 11 shows a side cross-sectional view of the snap-on surgical clip cartridge of FIG. 9 at line 9-9 in accordance with aspects of the disclosure.
Figure 12:
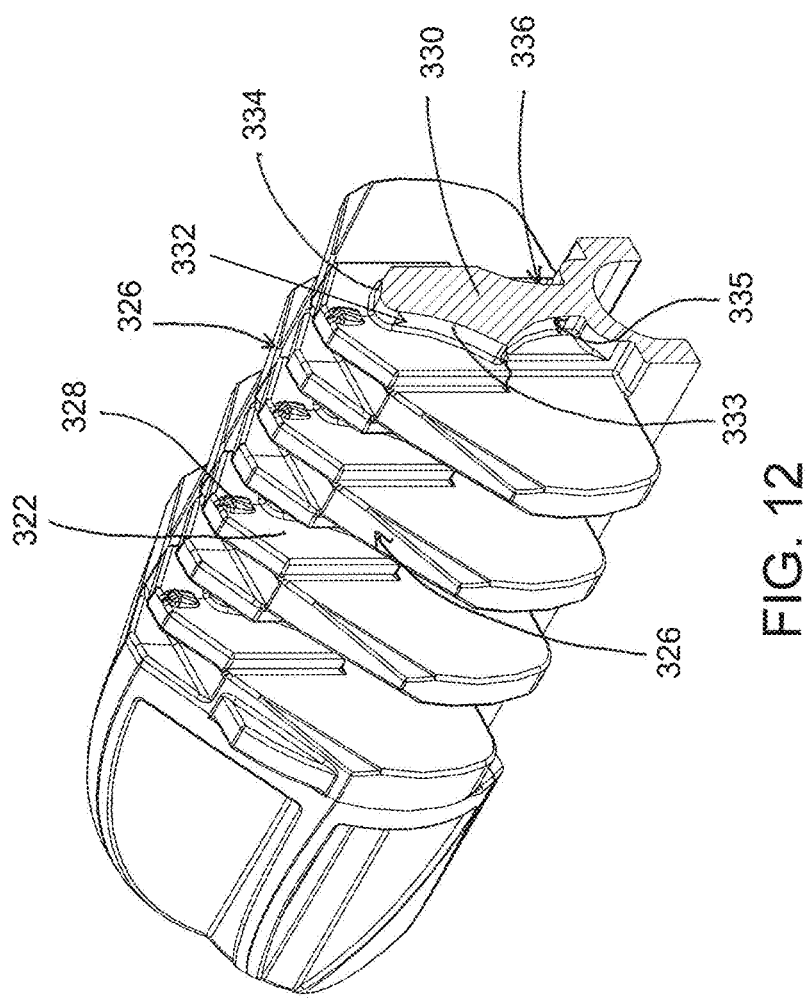
FIG. 12 shows a perspective cross-sectional view of the snap-on surgical clip cartridge of FIG. 9 at line 9-9 in accordance with aspects of the disclosure.
Figure 13:
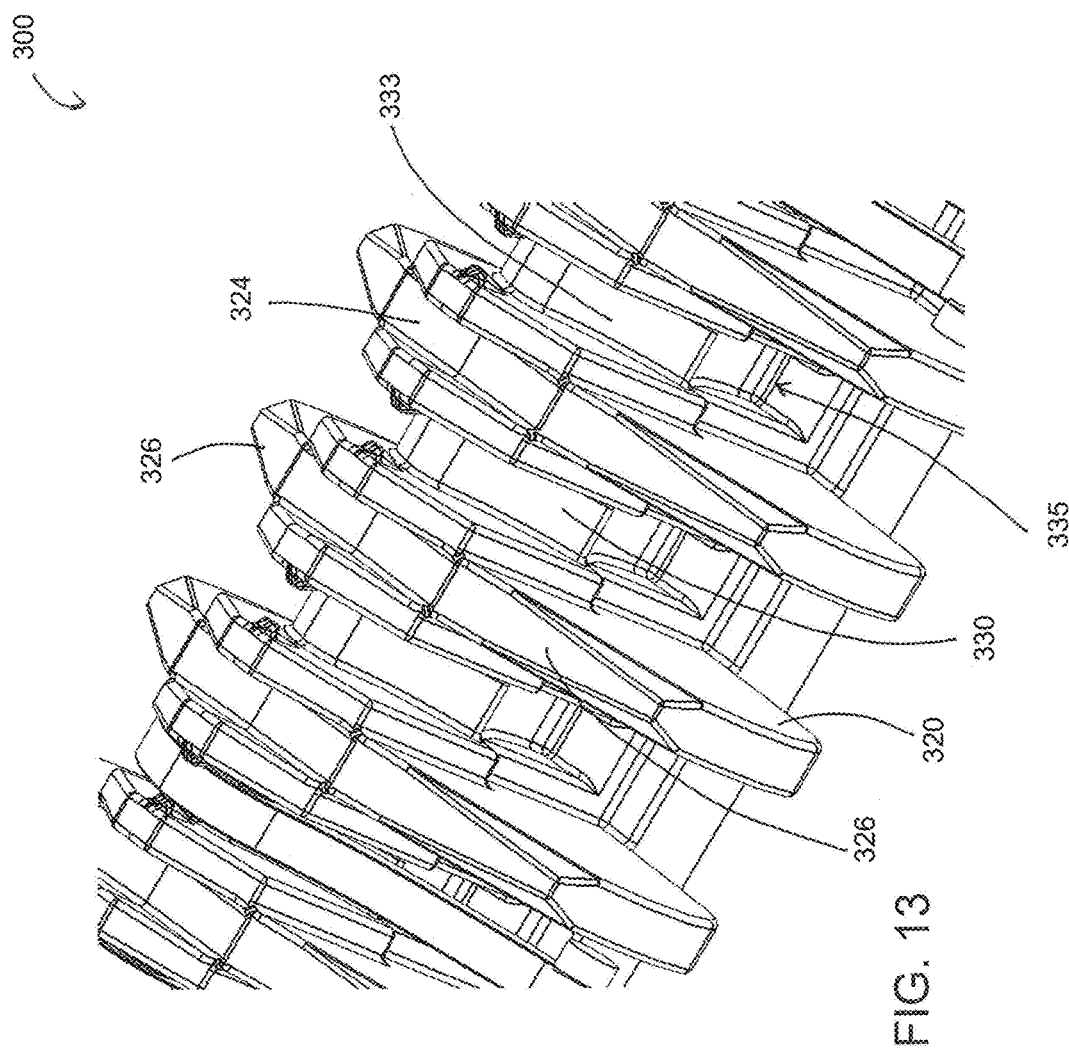
FIG. 13 shows a close-up perspective view of the snap-on surgical clip cartridge in accordance with aspects of the disclosure.

In one aspect, as best shown in FIGS. 11-13, the spacer portion 330 may define a top surface 332, and the top surface 332 may have a concave segment 333 and a convex segment 334. The concave segment 333 and a convex segment 334 may have a profile complementary to the inner convex surface 122 and the inner concave surface 112, respectively, of the surgical clip 100. The complementary profiles may help minimize unwanted displacement or play of the surgical clip 100, relative to the surgical clip cartridge 300, when the surgical clip 100 is being retrieved and withdrawn from the surgical clip cartridge 300. Additionally, or alternatively, the complementary profiles may assist in the loading of the surgical clips 100 onto surgical clip cartridge 300 by providing a limit or a stop as the surgical clips 100 are inserted downwardly towards the base portion 310.

In one aspect, as best shown in FIGS. 11 and 12, the spacer portion 330 may define at least one inwardly tapering section 335, 336. A depth of the inwardly tapering sections 335, 336 may increase when moving from an upper portion of the spacer towards a lower portion of the spacer portion 330 towards the base portion 310. In other words, the depth of the inwardly tapering sections 335, 336, relative to a central axis of the respective spacer portion 330, increases when moving from the top of the spacer portion 330 towards the base portion 310, as shown in FIG. 11. In one aspect, as the clip applier 200 is used to retrieve the surgical clip 100 from the surgical clip cartridge 300 (the trajectory of which is generally illustrated in FIGS. 14 and 15), the legs 110, 120 of the surgical clip 100 may be biased inward in order for the bosses 142, 144, 152, 154 to engage with the notches 212, 214, 222, 224 of the clip applier 200. The inwardly tapering section 335, 336 may enable the legs 110, 120 to flex a sufficient amount for the clip applier 200 to engage with the surgical clip 100. The clip applier 200 may then subsequently be maneuvered upwardly, against the latching protrusions 328 to disengage and release the surgical clip 100 from the surgical clip cartridge 300.

In one aspect, as shown in FIGS. 14 and 15, the surgical clip cartridge 300 may include nine dividers 320 and two end supporting walls 318, and the dividers 320 and supporting walls 318 may be used to retain up to ten surgical clips 100. In one aspect, the surgical clip cartridge 300 may be configured to retain between four to twenty surgical clips 100. In one aspect, surgical clip cartridge 300 may be configured to retain four and twelve surgical clips 100.

Figure 5:
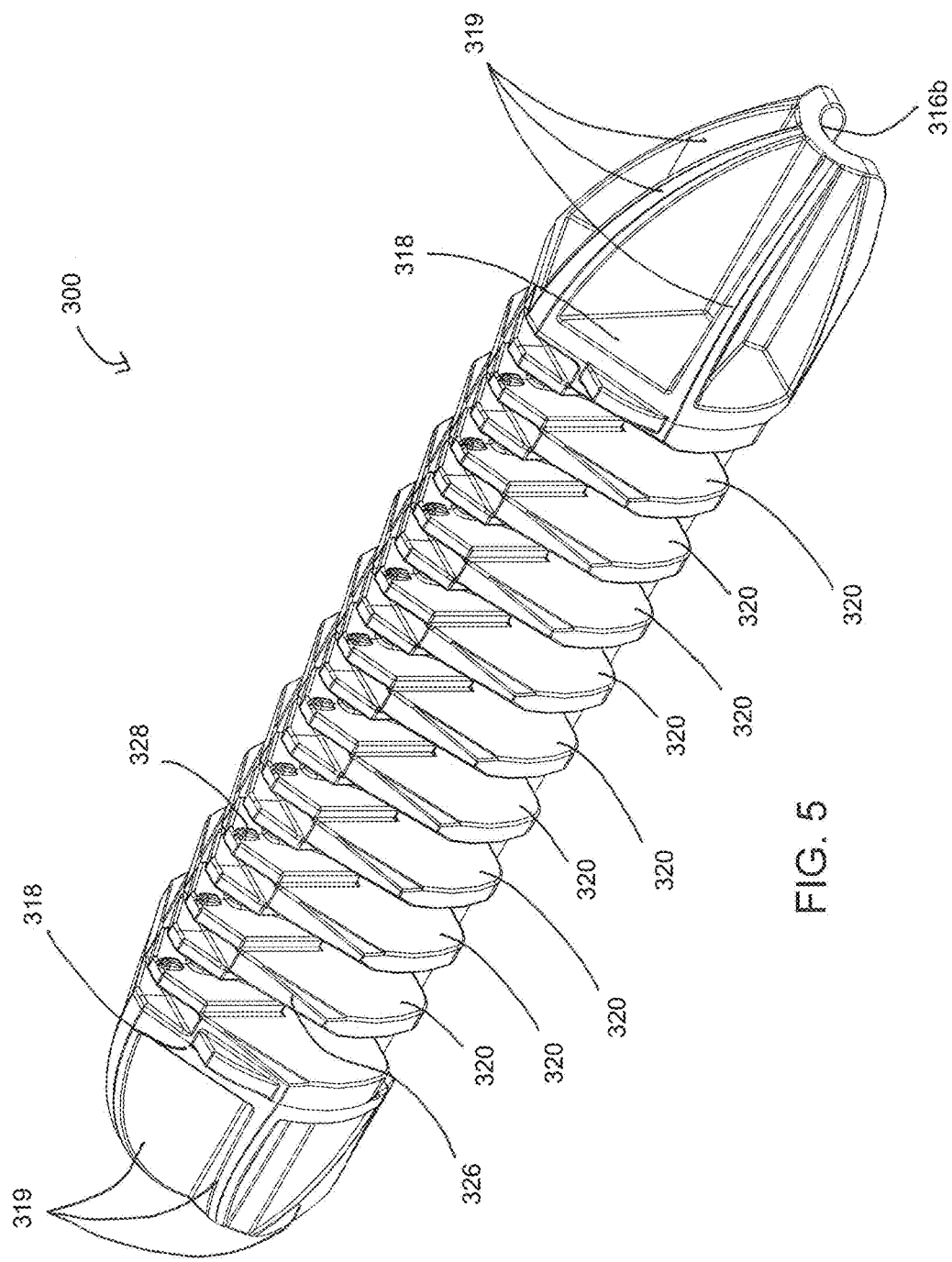
FIG. 5 shows a top perspective view of a snap-on surgical clip cartridge in accordance with aspects of the disclosure.
Figure 7:
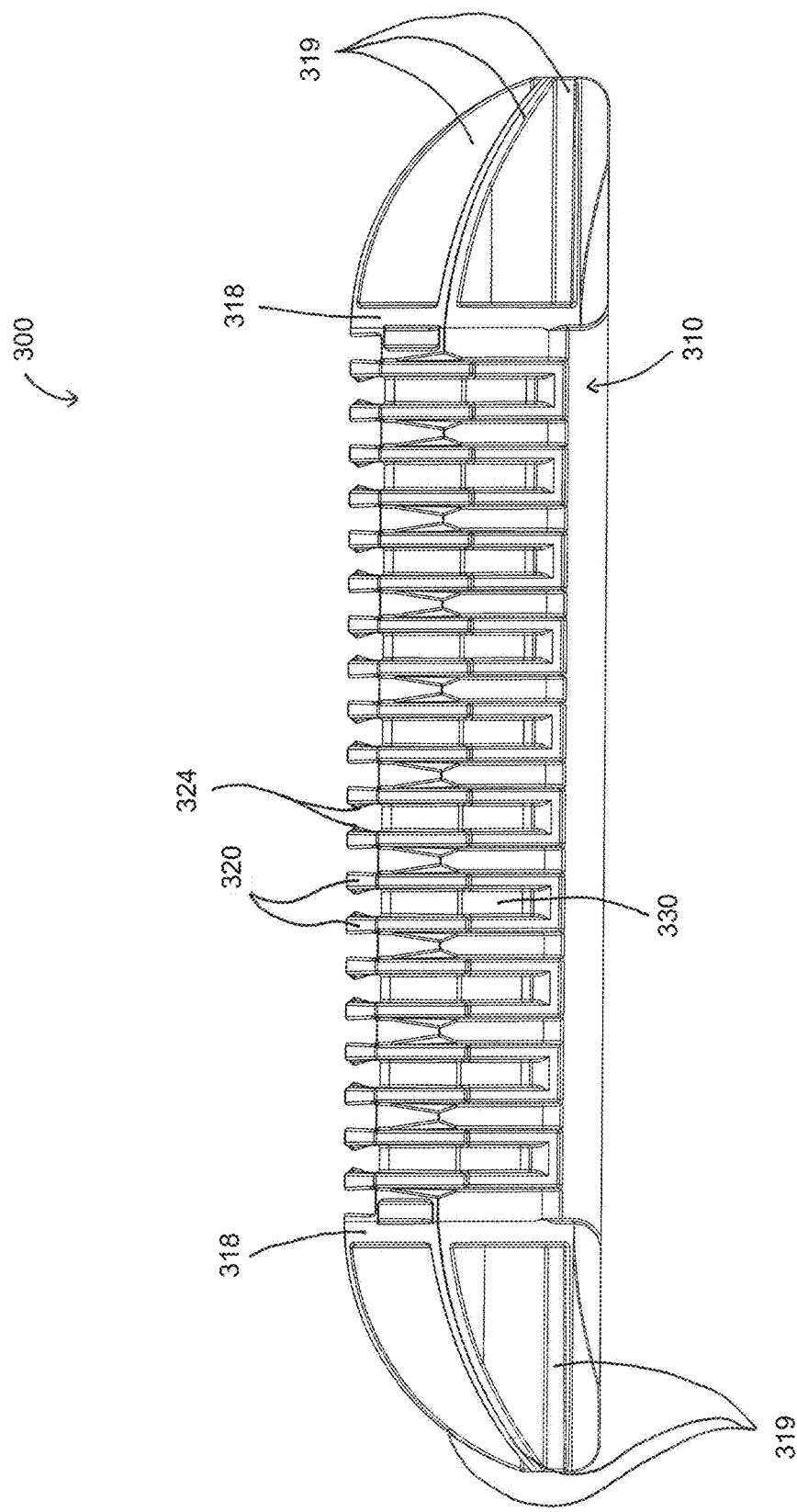
FIG. 7 shows a front view of the snap-on surgical clip cartridge of FIG. 1 in accordance with aspects of the disclosure.
Figure 8:
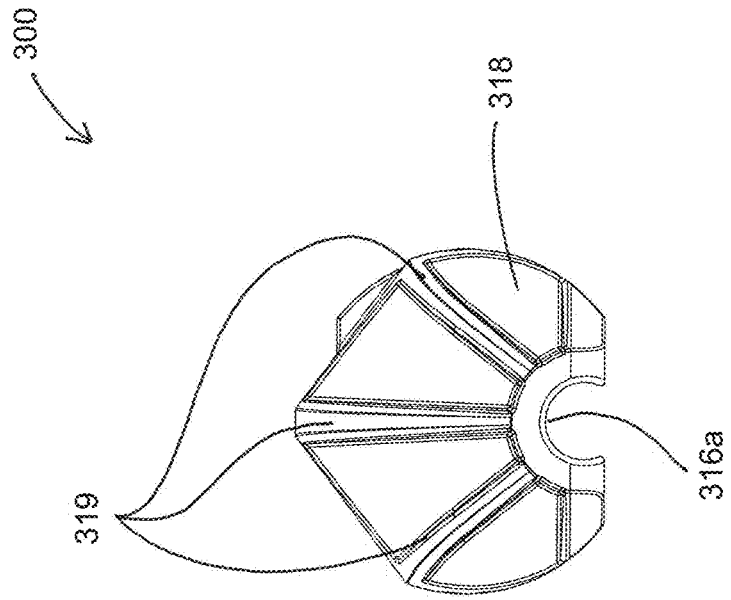
FIG. 8 shows a side view of the snap-on surgical clip cartridge of FIG. 1 in accordance with aspects of the disclosure.

In one aspect, as shown in FIGS. 5, 7, and 9, a plurality of ribs 319 may be provided between the end supporting walls 318 and the docking portion 316a, 316b. The plurality of ribs 319 may define a convex or curvilinear tapering profile that narrows towards extreme longitudinal ends of the surgical clip cartridge 300. The tapering ribs 319 may promote insertion and removal of the clip cartridge 300 into and out of the body cavity during a surgical operation. The tapering ribs 319 may further promote or enable flexing of the docking portion 316a, 316b when the surgical clip cartridge 300 is snapped-on or snapped-off of the surgical instrument shaft.

Referring back to FIG. 6, the surgical clip cartridge 300 may include one or more light sources 340, which may be used to illuminate the body cavity during a surgical procedure. The one or more light sources 340 may be in the form of light-emitted diodes, however, other illumination sources are of course contemplated as will be appreciated by one skilled in the art in view of the present disclosure. For example, other illumination sources may include, but are not limited to, incandescent light, UV light, infrared light, and luminescence. The one or more light sources 340 may be powered by a sealed internal battery housed within the surgical clip cartridge 300. The one or more light sources 340 may further be connected to one or more electrical switches 350, 360 located on the surgical clip cartridge 300. Alternatively, the one or more light sources 340 may be powered externally via electrical contacts on the surgical clip cartridge 300 that may be connected to corresponding electrical contacts on the surgical tool shaft (not shown). An electric switch may further be provided on a handle attached to the surgical tool shaft to actuate the one or more light sources 340.

In one aspect, the one or more light sources 340 may be primarily aimed at directions other than a direction in which the surgical clips are retrieved and removed from the surgical clip cartridge 300 to prevent glare. In particular, where visual sight of the surgical clips via a camera or other visual means within the body cavity is needed during retrieval from the surgical clip cartridge, the orientation of the one or more light sources 340 away from a direction of retrieval may prevent light from being directed towards the camera or other visual means. Instead, the one or more light sources 340 may be directed in other directions to provide general illumination within the body cavity. Additionally or alternatively, the one or more light sources 340 may be oriented to direct light towards a distal end of the surgical tool shaft, when the surgical clip cartridge is mounted to the surgical tool shaft, in order to provide illumination to a surgical area, particularly when the surgical tool shaft is installed with an end effector for performing a surgical procedure, as will be appreciated by one skilled in the art in view of the present disclosure.

In one aspect as shown in FIG. 6, the electrical switch 350 may be located on a mounting surface of the at least one docking portion 316a, 316b. The electrical switch 350 may be actuated or depressed as the surgical clip cartridge 300 is mounted onto the surgical instrument shaft via the at least one docking portion 316a, 316b. Once the switch 350 is actuated or depressed, the one or more light sources 340 may be activated to provide illumination. The electrical switch 350 may subsequently be released by removing the surgical clip cartridge 300 from the surgical instrument shaft thereby deactivating the one or more light sources 340.

Additionally or alternatively, the electrical switch 360 may be disposed on a distal or proximal end of the base portion 310. The electrical switch 360 may be actuated manually be an operator prior to, during, or after the surgical clip cartridge 300 has been mounted to the surgical instrument shaft. By actuating the electrical switch 360, the one or more light sources 340 may be activated to provide illumination. The electrical switch 360 may be actuated again to deactivate the one or more light sources 340.

Turning to FIGS. 16-22, a second exemplary surgical clip cartridge 400 is shown. The surgical clip cartridge 400 may include a generally elongated circular or elliptical body 410 extending in a longitudinal direction. The body 410 may define a mounting groove 414 for attaching the body 410 onto a surgical instrument. The mounting groove 414 may extend along the longitudinal direction. The mounting groove 414 may include at least one docking portion 416a, 416b, and the at least one docking portion 416a, 416b may define a concave semi-circular surface configured to conform around the surgical instrument shaft. In one aspect, the concave semi-circular surface may have a first radius, and the first radius may be less than or equal to an outer radius of the surgical instrument shaft in order to provide an interference fit when the docking portion 416a, 416b is attached to the surgical instrument shaft. The concave semi-circular surface may revolve about a central longitudinal axis of the docking portion 416a, 416b, and the revolution of the concave semi-circular surface may be greater than or equal to 180°. In one aspect, the angle of revolution is between about 180° to 270°. For example, the angle of revolution of the concave semi-circular surface may be between about 185° to 270°, or between about 220° to 245° to ensure a secure fit about the surgical instrument shaft, when attached, while enabling the surgical clip cartridge 400 to be snapped-on or snapped-off of the surgical instrument shaft using the force of a user's hands, for example. It will be appreciated by one skilled in the art, in view of the present disclosure, that the arc length and the revolution of the arc may be selected based on a size or radius of the surgical instrument shaft that the surgical clip cartridge 400 is intended to attach on to. Additionally or alternatively, the arc length and the revolution of the arc may be selected based on the material properties of the surgical clip cartridge 400, such as the resiliency, to ensure that the at least one docking portion 416a, 416b may displace sufficiently to engage and secure the surgical clip cartridge 400 to the surgical instrument shaft without damage or failure during the product life.

In one aspect, the concave semi-circular surface of the at least one docking portion 316a, 316b may include one or more of a friction material, knurling, notches, and protrusions to prevent axial or rotational displacement when the docking portion 416a, 416b is attached to the surgical instrument shaft. The addition of one or more of the above surface features may prevent the body 410 from shifting relative to the surgical instrument shaft, thereby promoting accuracy and repeatability when a surgeon attempts to retrieve a clip 100 from the surgical clip cartridge 400 during a surgical procedure. In one aspect, the docking portion 416a, 416b and the surgical instrument shaft may include corresponding ribs and grooves to prevent axial and/or radial movement of the surgical clip cartridge 400 relative to the surgical instrument shaft once the surgical clip cartridge 400 has been mounted to the surgical instrument shaft.

In one aspect, the body 410 may define a plurality of clip slots 420 arranged end-to-end relative to one another. Each of the clip slots 420 may be configured to receive and/or dispense the surgical clip 100 in a direction that is perpendicular to the longitudinal direction. In one aspect, the clip slots 420 may include a central portion 422 and an outer portion 424. The central portion 422 may include at least two latching protrusion 428 to interface with the latching orifice 135 of the surgical clip 100. In one aspect, the body 410 may include a total of four clip slots 420. However, it will be appreciated by one skilled in the art in view of the present disclosure, that the number of clip slots 420 provided on the body 410 may be selected based on the number of clips desired for a surgical operation and/or the available length provided on the surgical instrument shaft. In one aspect, the body 410 may have between four and twenty clip slots. In one aspect, the body 410 may have between four and eight clip slots.

Figure 20:
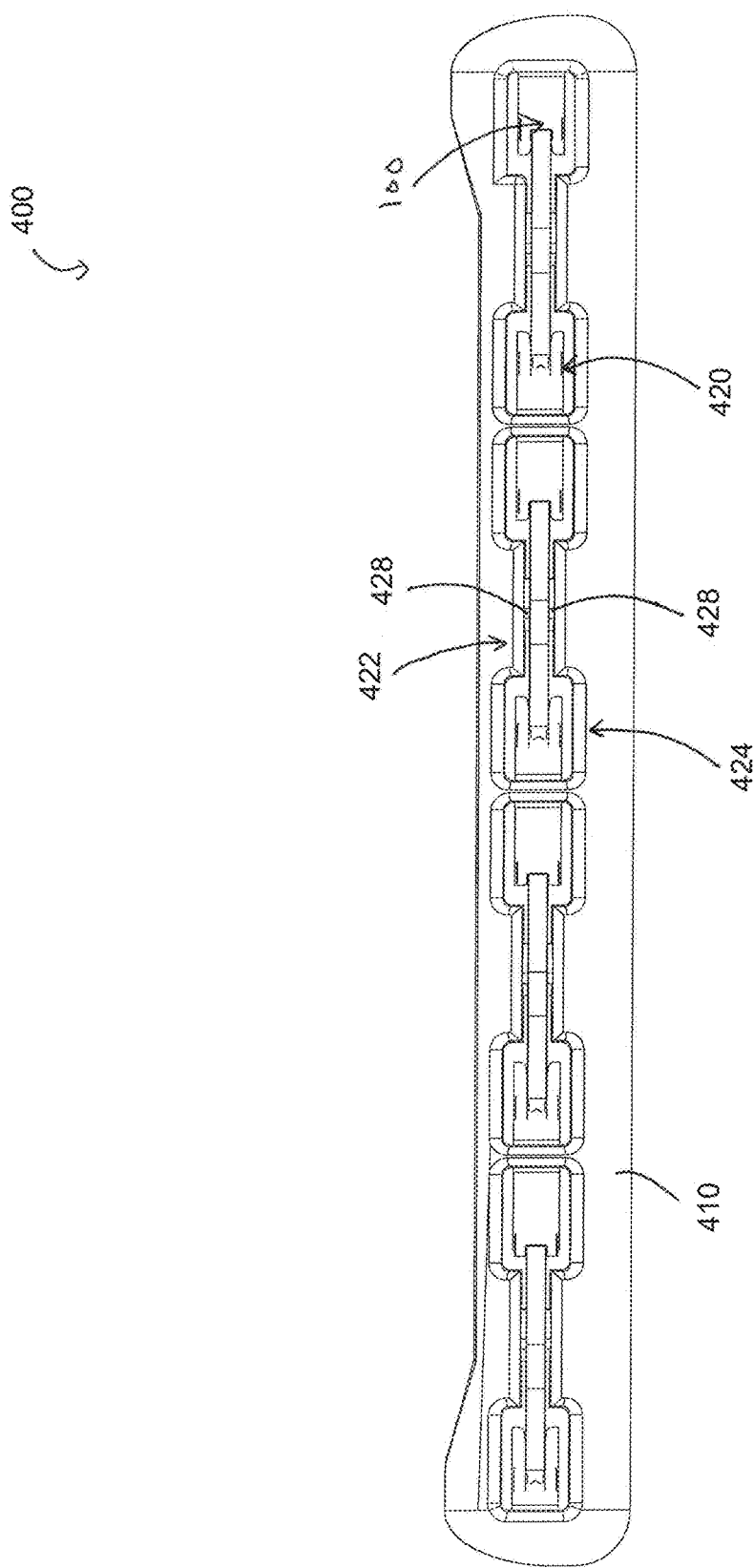
FIG. 20 shows a front view of the snap-on surgical clip cartridge of FIG. 16 in accordance with aspects of the disclosure.
Figure 21:
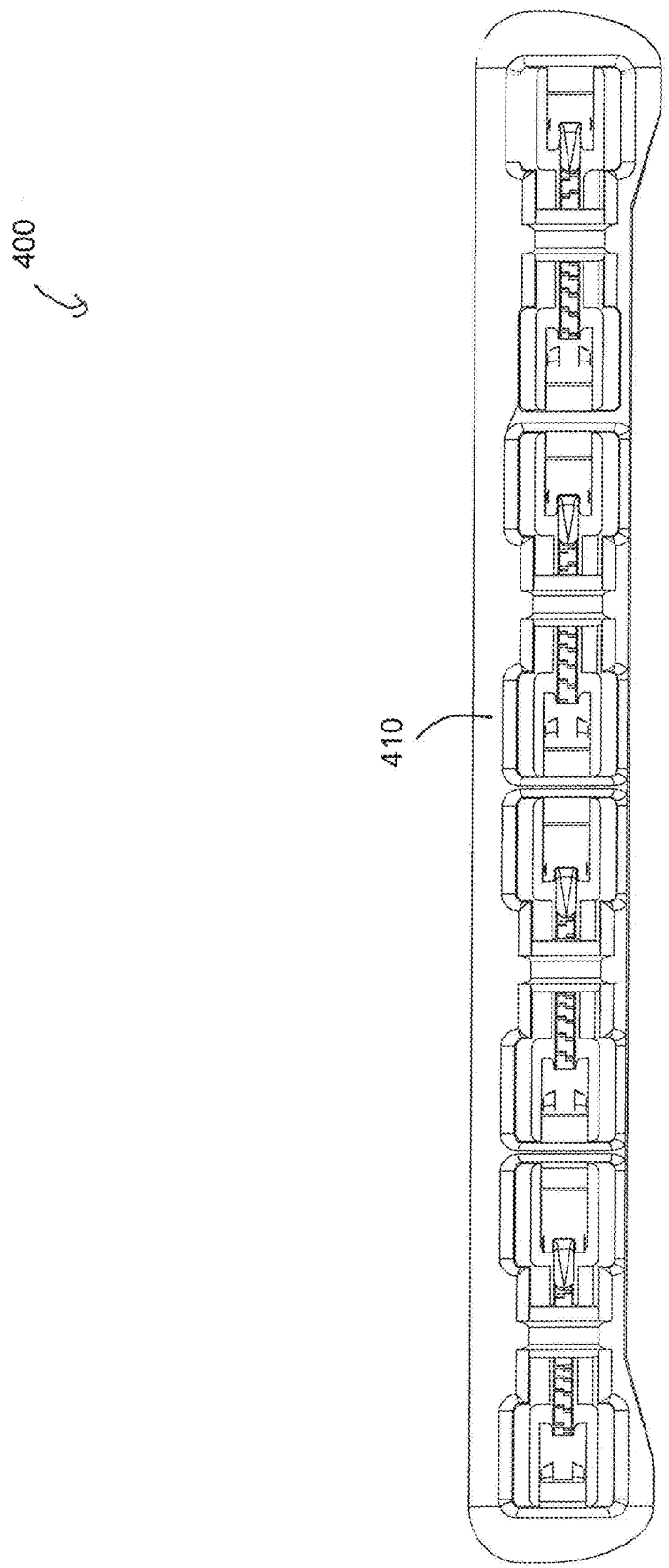
FIG. 21 shows a rear view of the snap-on surgical clip cartridge of FIG. 16 in accordance with aspects of the disclosure.

As shown in FIGS. 16 and 20, one surgical clip 100 may be stored within each of the clip slots 420, and the clip applier 200 may be inserted into the clip slots 420 to retrieve the surgical clip 100 retained therein. Once the clip applier 200 has been inserted into one of the clip slots 420, the clip applier 200 may be positioned about the surgical clip 100. In one aspect, the notches 212, 214 of the first jaw 210 may be configured to receive and lock the bosses 142, 144 of the first leg 110, and the notches 222, 224 of the second jaw 220 may be configured to receive and lock the bosses 152, 154 of the second leg 120. Alternatively, the notches 212, 214 of the first jaw 210 may be configured to receive and lock the bosses 152, 154 of the second leg 120, and the notches 222, 224 of the second jaw 220 may be configured to receive and lock the bosses 142, 144 of the first leg 110. The clip applier 200 may then be withdrawn from the clip slot 420. During the withdrawal process, the surgical clip 100 may be disengaged from the surgical clip cartridge 400 once a predetermined threshold force is applied to the surgical clip 100, via the clip applier 200 for example, such that the surgical clip 100 may be released from the latching protrusion 428.

In one aspect, as shown in FIGS. 16-19, a proximal and distal ends 418a, 418b of the surgical clip cartridge 400 may be rounded, filleted, and/or chamfered to promote insertion and removal of the clip cartridge 400 into and out of the body cavity during a surgical operation.

Referring back to FIG. 16, the surgical clip cartridge 400 may include one or more light sources 440, which may be used to illuminate the body cavity during a surgical procedure. The one or more light sources 435 may be in the form of light-emitted diodes, however, other illumination sources are of course contemplated as will be appreciated by one skilled in the art in view of the present disclosure. For example, other illumination sources may include, but are not limited to, incandescent light, UV light, infrared light, and luminescence. The one or more light sources 435 may be powered by a sealed internal battery housed within the surgical clip cartridge 400. The one or more light sources 440 may further be connected to an electrical switch 440 located on the surgical clip cartridge 400. Alternatively, the one or more light sources 435 may be powered externally via electrical contacts on the surgical clip cartridge 400 that may be connected to corresponding electrical contacts on the surgical tool shaft (not shown). An electric switch may further be provided on a handle attached to the surgical tool shaft to selectively actuate the one or more light sources 435.

Figure 18:
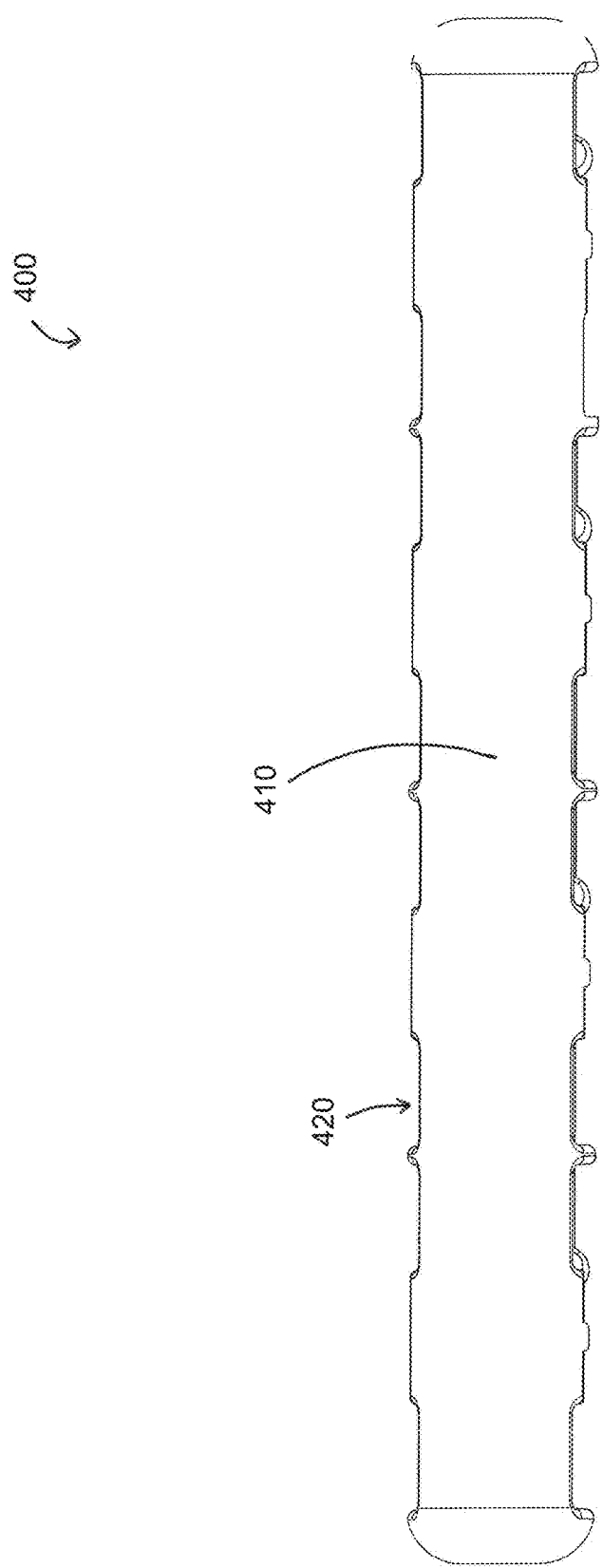
FIG. 18 shows a bottom view of the snap-on surgical clip cartridge of FIG. 16 in accordance with aspects of the disclosure.
Figure 19:
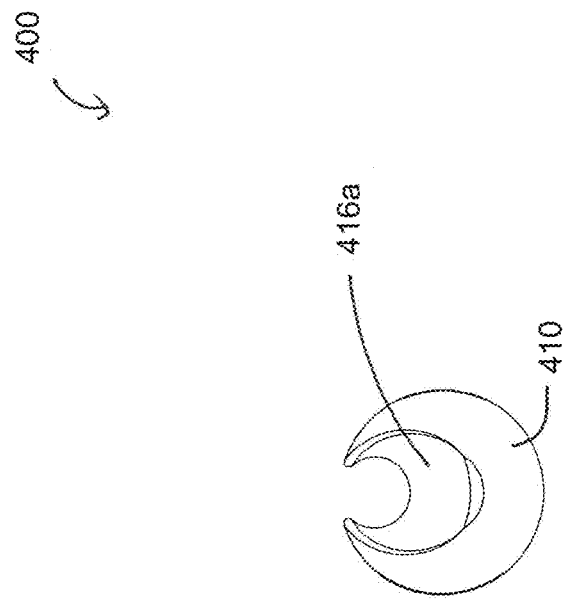
FIG. 19 shows a side view of the snap-on surgical clip cartridge of FIG. 16 in accordance with aspects of the disclosure.

In one aspect, the one or more light sources 435 may be primarily aimed at directions other than a direction in which the surgical clips are retrieved from the surgical clip cartridge 400 to prevent glare. As shown in FIGS. 16 and 18, the one or more light sources 435 may be oriented to direct light towards a distal and/or proximal end of the surgical tool shaft, when the surgical clip cartridge is mounted to the surgical tool shaft, in order to provide illumination to a surgical area, particularly when the surgical tool shaft is installed with an end effector for performing a surgical procedure, as will be appreciated by one skilled in the art in view of the present disclosure.

In one aspect, the electrical switch 440 may be located on a mounting surface of the at least one docking portion 416a, 416b. The electrical switch 440 may be actuated or depressed as the surgical clip cartridge 400 is mounted onto the surgical instrument shaft via the at least one docking portion 416a, 416b. Once the switch 440 is actuated or depressed, the one or more light sources 440 may be activated to provide illumination. The electrical switch 440 may subsequently be released by removing the surgical clip cartridge 400 from the surgical instrument shaft thereby deactivating the one or more light sources 435.

Figure 23:
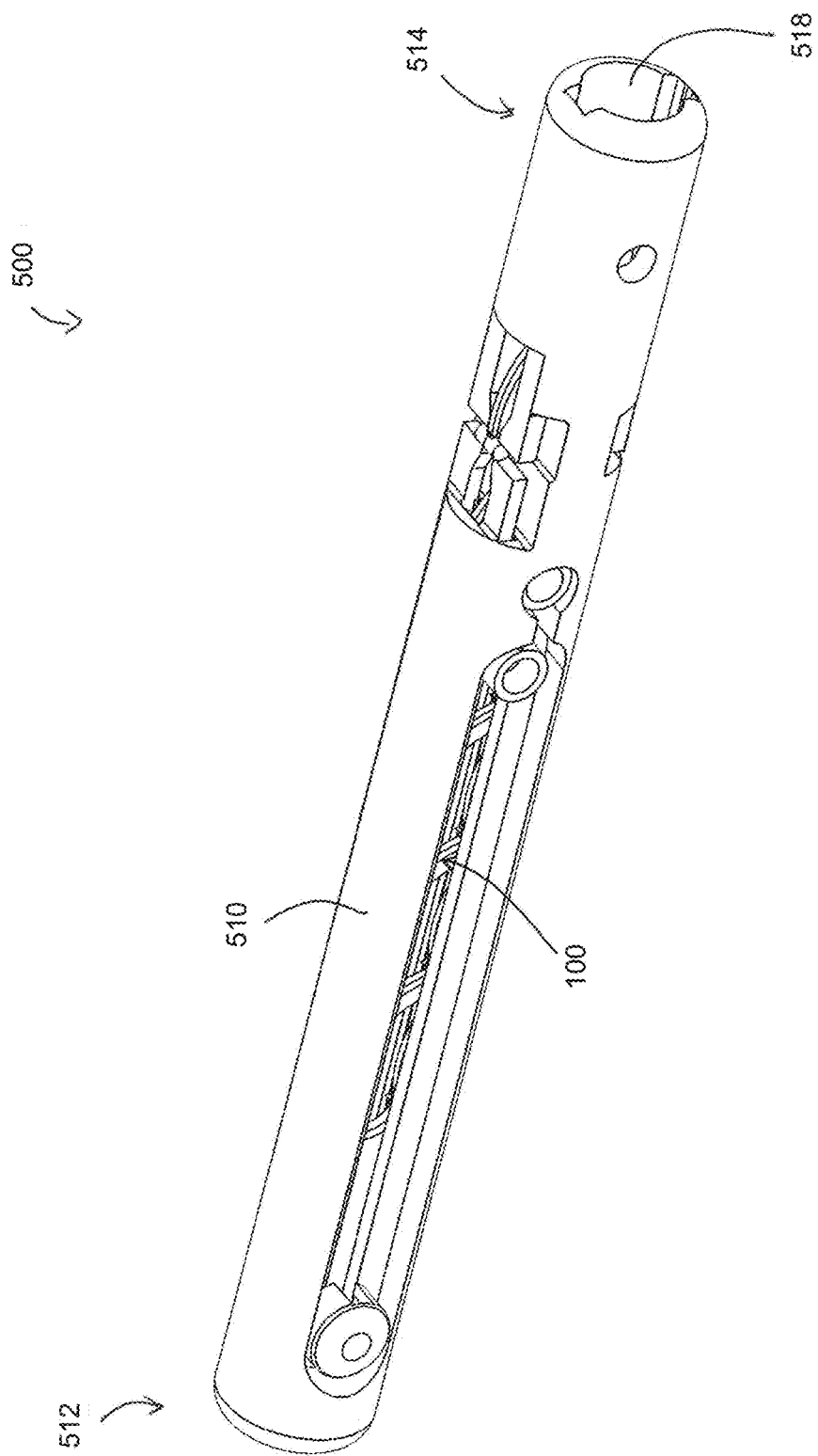
FIG. 23 shows a front perspective view of a surgical clip cartridge in accordance with aspects of the disclosure.
Figure 24:
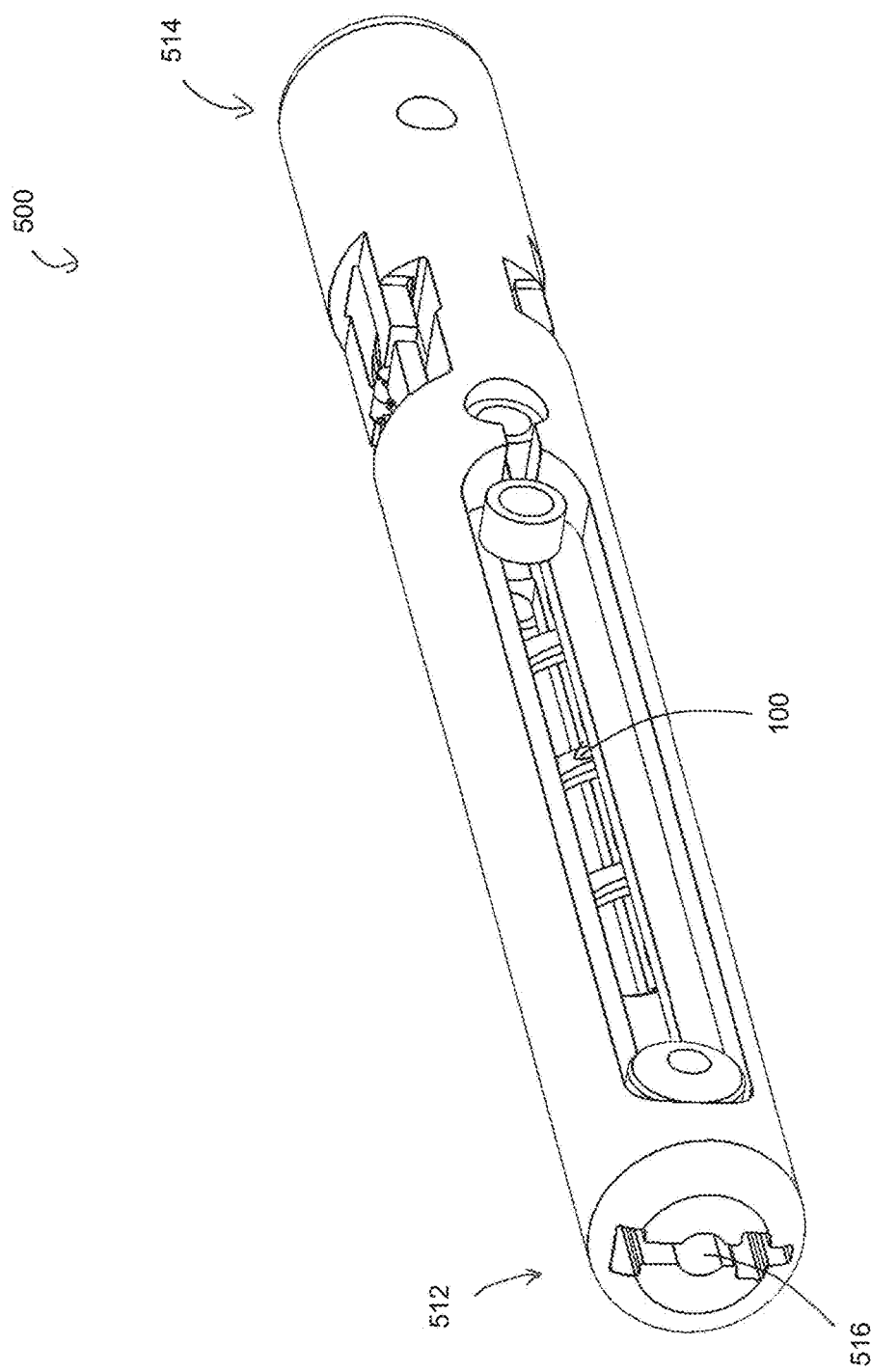
FIG. 24 shows a rear perspective view of the surgical clip cartridge of FIG. 23 in accordance with aspects of the disclosure.

Turning to FIGS. 23 and 24, a third exemplary surgical clip cartridge 500 is shown. The surgical clip cartridge 500 may include a generally elongated circular or elliptical body 510 extending in a longitudinal direction. The circular or elliptical body 510 may include a proximal end 512 and a distal end 514. The proximal end 512 may include a tool engaging slot 516 configured to receive and lock a distal end of a surgical tool shaft. The distal end of the surgical tool shaft may include lateral protrusions for insertion into the tool engaging slot 516 and to enable both the surgical tool shaft and the surgical clip cartridge 500. The distal end 514 of the surgical clip cartridge 500 may include a clip feeding slot 518 configured to receive and dispense clips, such as but not limited to surgical clips 100 discussed above. Of course, other types of clips may be used with the surgical clip cartridge 500.

In one aspect, the surgical clip cartridge 500 is configured to store a plurality of surgical clips 100, sequentially in abutting fashion, within an interior lumen or chamber of the surgical clip cartridge 500. A spring mechanism may be provided to advance the surgical clips 100 toward the clip feeding slot 518 as a preceding surgical clip 100 is removed.

The surgical clips 100 may be removed from the clip feeding slot 518 by inserting the pair pivotable jaws 210, 220 of the clip applier 200 into then clip feeding slot 518, generally in the longitudinal direction. The pair pivotable jaws 210, 220 may then engage the bosses 142, 144, 152, 154. The outermost surgical clip 100 may then be withdrawn from the clip feeding slot 518 using the clip applier 200.

Figure 22:
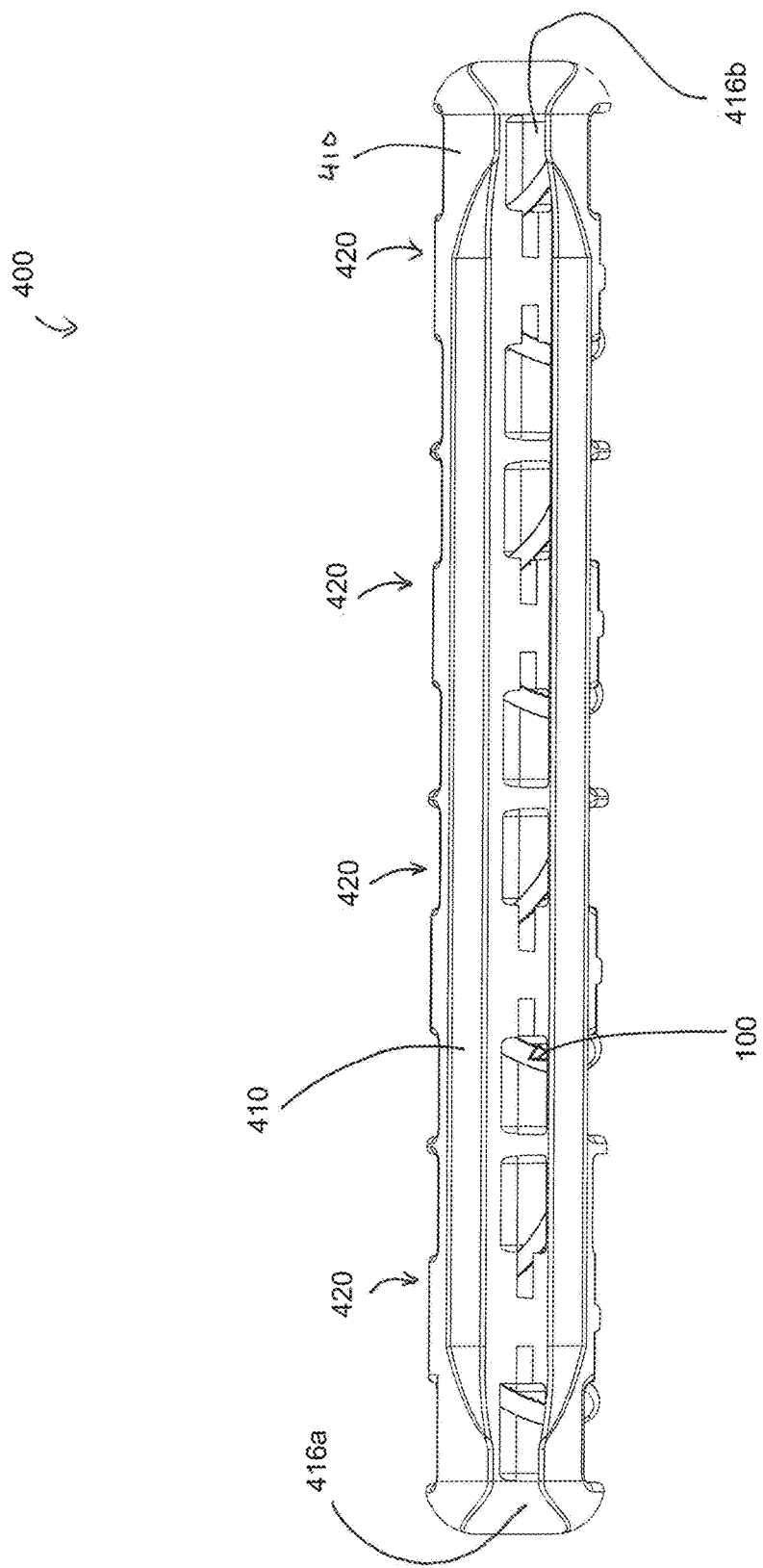
FIG. 22 shows a top view of the snap-on surgical clip cartridge of FIG. 16 in accordance with aspects of the disclosure.

In one aspect, as shown in FIGS. 22 and 23, the proximal end 512 and the distal end 514 of the surgical clip cartridge 500 may be rounded, filleted, and/or chamfered to promote insertion and removal of the clip cartridge 500 into and out of the body cavity during a surgical operation.

Figure 25:
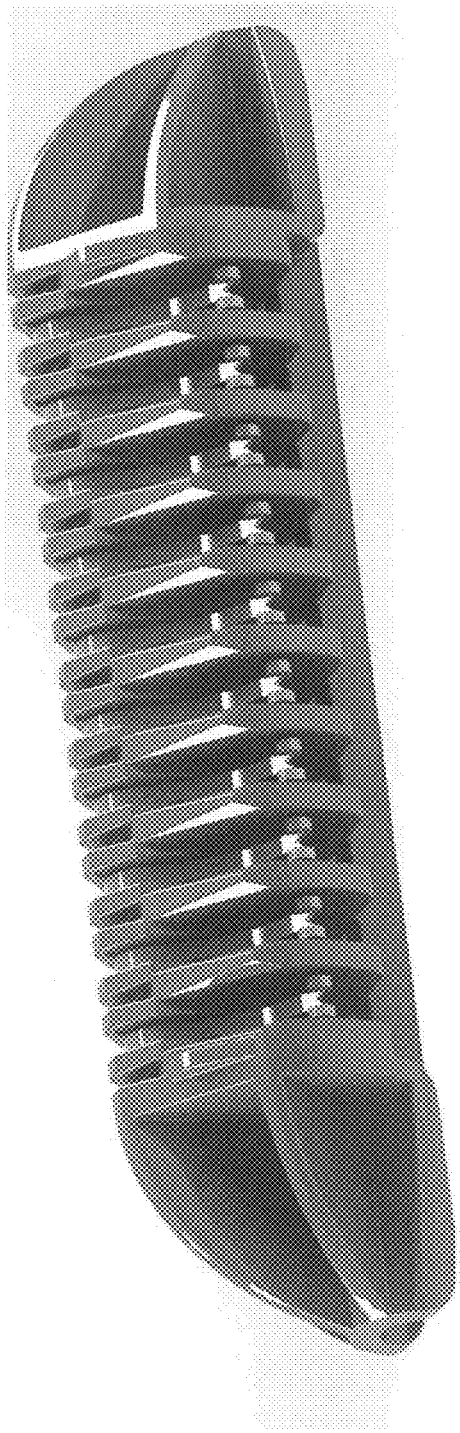
FIG. 25 shows a three-dimensional rendering of the snap-on surgical clip cartridge of FIG. 1 in accordance with aspects of the disclosure.
Figure 26:
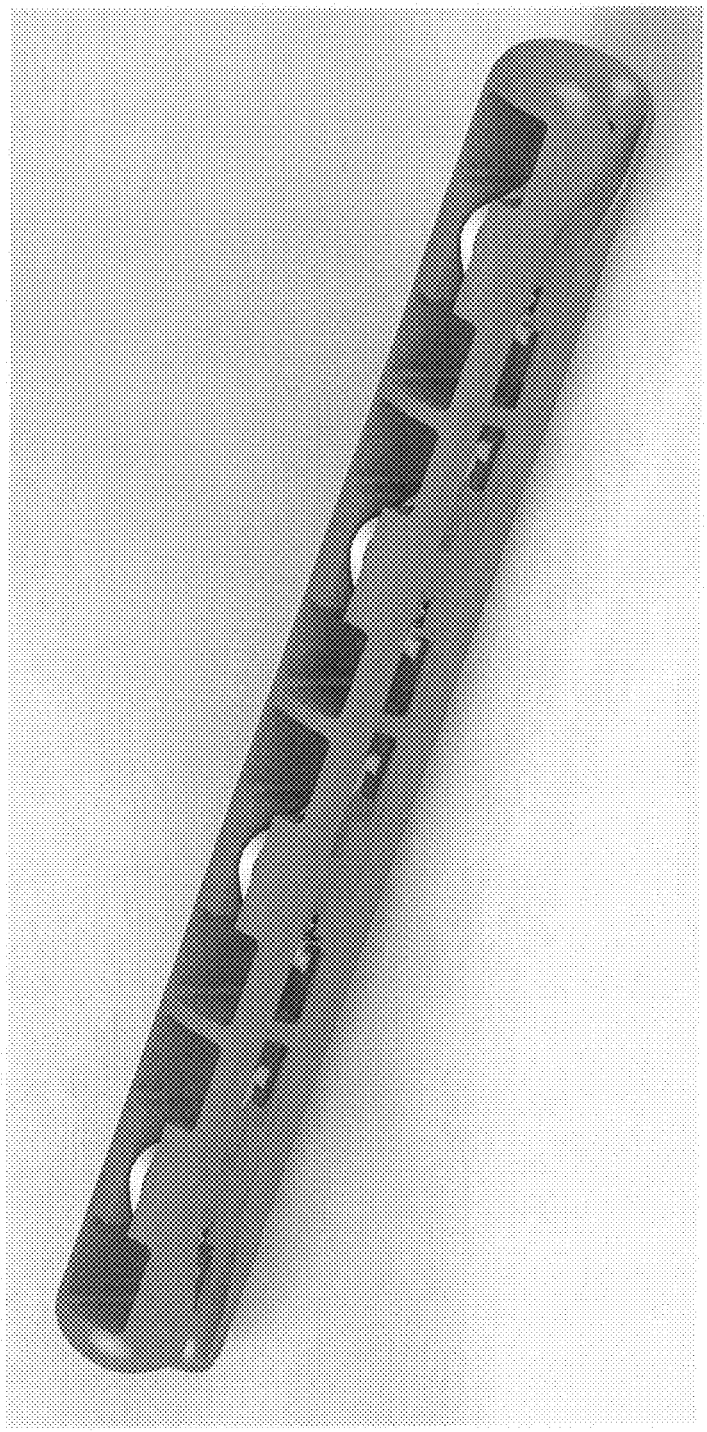
FIG. 26 shows a three-dimensional rendering of the snap-on surgical clip cartridge of FIG. 16 in accordance with aspects of the disclosure.
Figure 27:
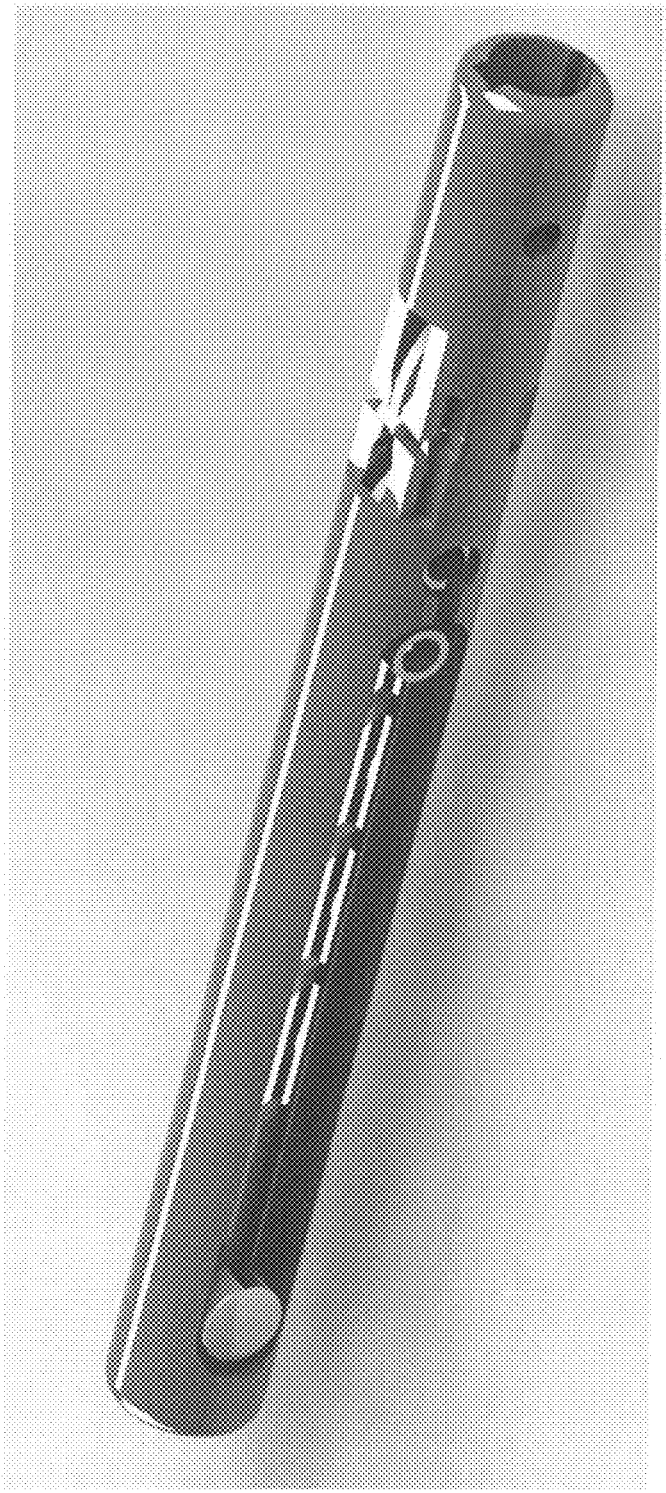
FIG. 27 shows a three-dimensional rendering of the surgical clip cartridge of FIG. 23 in accordance with aspects of the disclosure.
Figure 28:
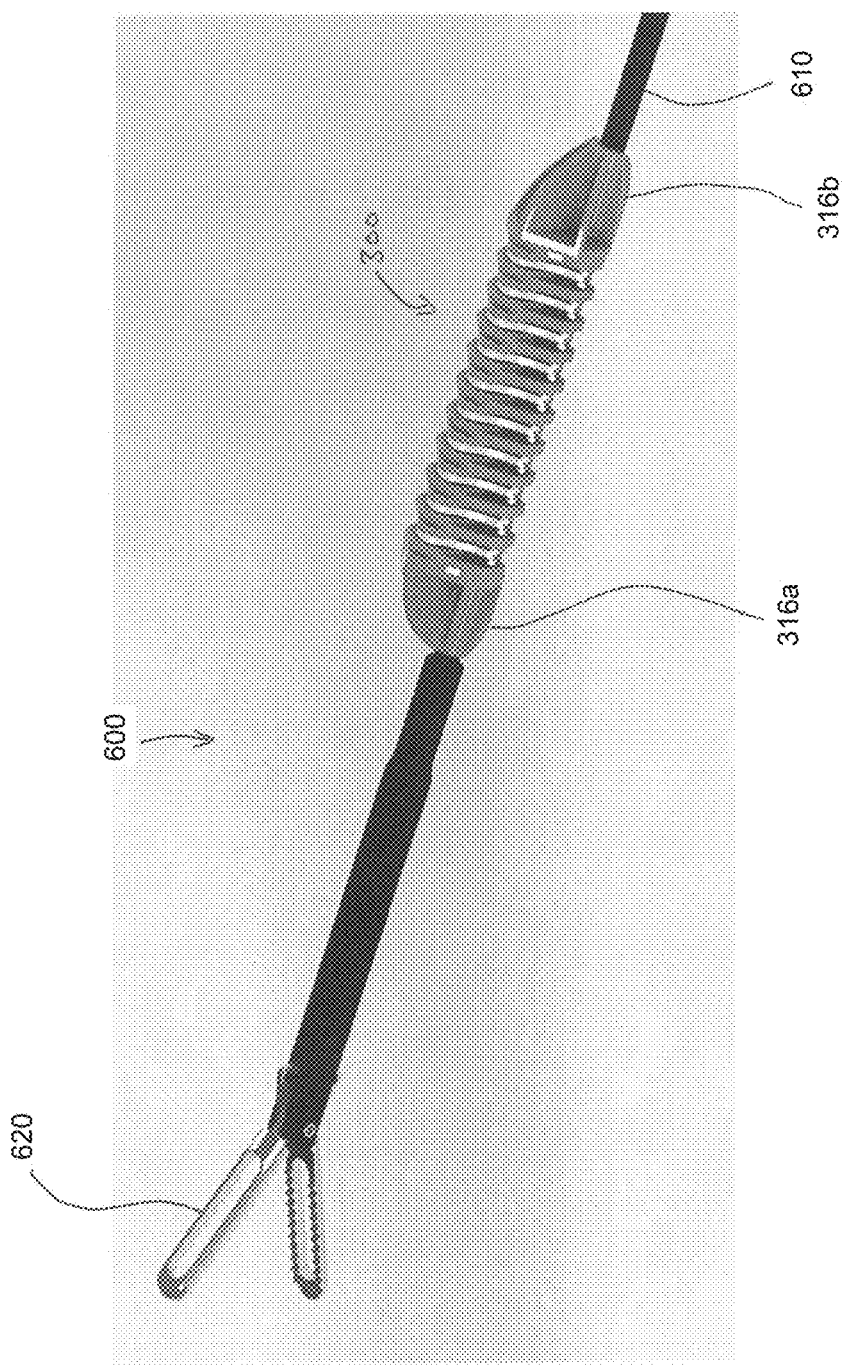
FIG. 28 shows a surgical assembly including a surgical clip cartridge attached to a surgical instrument in accordance with aspects of the disclosure.

FIGS. 25, 26, and 27 show three-dimensional renderings of the first surgical clip cartridge 300, second surgical clip cartridge 400, and third surgical clip cartridge 500, respectively. FIG. 28 shows a surgical assembly comprising a surgical tool 600 with an elongated shaft 610 and an end effector 620 disposed at a distal end of the elongated shaft 610. In one aspect, the end effector may be a grasper. In one aspect, any one or more of the first surgical clip cartridge 300, second surgical clip cartridge 400, and third surgical clip cartridge 500, may be attached to the elongated shaft 610. As specifically shown in FIG. 26, the first surgical clip cartridge 300 is attached to the elongated shaft 610 via the at least one docking portion 316a, 316b, as described above. In one aspect, a diameter of the elongated shaft 610 may be between 1 mm and 100 mm.

A system and a method of using a surgical clip cartridge during a surgical procedure will now be discussed. In one aspect, the surgical procedure may be minimally invasive surgery (such as micro-laparoscopic or needlescopic surgery) where instruments and/or accessories may be introduced into a body cavity through relatively small ports to reduce pain, improve recovery time, and minimize scarring. The small ports may be less than 3 mm in diameter, and in select aspects may be between 1 mm to 3 mm. The use of such small ports may help minimize triangulation issues and improve maneuverability in comparison with surgical operations where multiple instruments are inserted in parallel through a single larger opening. Even with the use of smaller ports, a single larger port may be provided to pass larger components into the body cavity, such an interchangeable end effector.

Figure 29A:
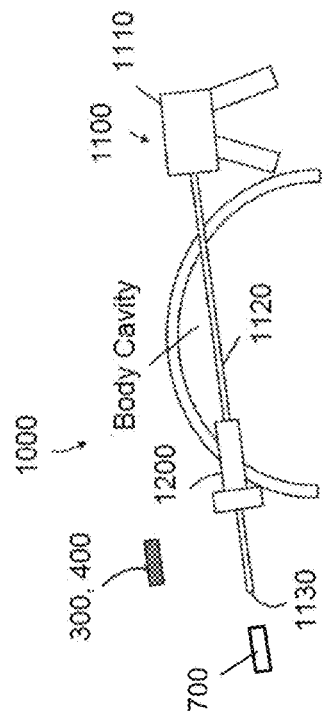
FIGS. 29A-29H show an exemplary method of using the surgical clip cartridge in a procedure in accordance with aspects of the disclosure.

Referring to FIGS. 29A-29H, an exemplary micro-laparoscopic system 1000 including a snap-on surgical clip cartridge, such as the surgical clip cartridge 300, 400, 500 discussed above, is shown. As shown in FIG. 29A, the micro-laparoscopic system 1000 may include a surgical tool 1100 and an access port 1200. The surgical tool 1100 may comprise a handle portion 1110 and an elongated needle shaft 1120. The elongated needle shaft 1120 may have a maximal outer diameter of 3 mm, and in one aspect, the diameter of the elongated needle shaft 1120 is between 1 mm and 3 mm. The elongated needle shaft 1120 may include a needle tip 1130 located at a distal end thereof. The needle tip 1130 may be a beveled or sharp needle tip configured to puncture through body tissue and may be used to puncture through a body wall and into a body cavity.

In one aspect, the needle tip 1130 of the surgical tool 1100 may be directed adjacent to a body cavity wall. Pressure in a distal direction may be applied to the elongated needle shaft 1120 and the needle tip 1130. As pressure is being applied to the body cavity wall via the needle tip 1130, an incision or opening 1250 may be formed in the body cavity wall. As the incision or opening 1250 is formed, the needle tip 1130 and at least a portion of the elongated needle shaft 1120 may be advanced to enter into the body cavity.

The access port 1200 may be provided at a location remote from the incision or opening 1250. In one aspect, the access port 1200 may define an interior lumen with a maximal internal diameter of between 3 mm to 30 mm. In one aspect, the access port 1200 may be introduced and employed through an umbilicus of the patient. Once the access port 1200 has been positioned in and/or on the body wall, and once the elongated needle shaft 1120 has been inserted into the body cavity via the incision or opening 1250, the needle tip 1130 and the elongated needle shaft 1120 may be guided from inside the body cavity to an external environment outside the body cavity, by entering a distal end of the access port 1200, passing through the interior lumen of the access port 1200, and exiting a proximal end of the access port 1200 as generally shown in FIGS. 29A and 29B.

Figure 29B:
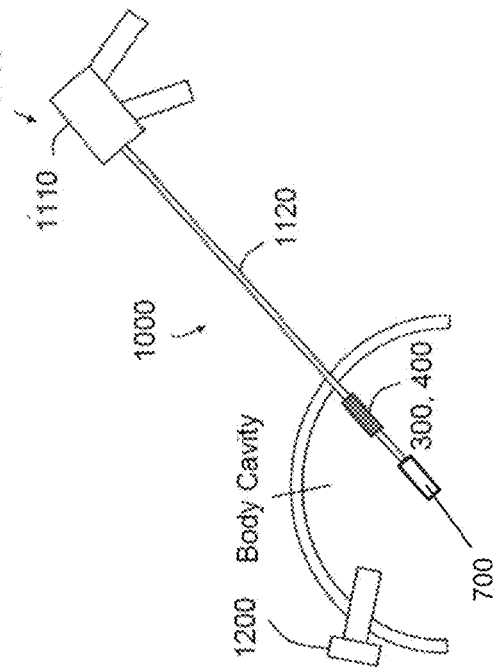
Figure 29C:
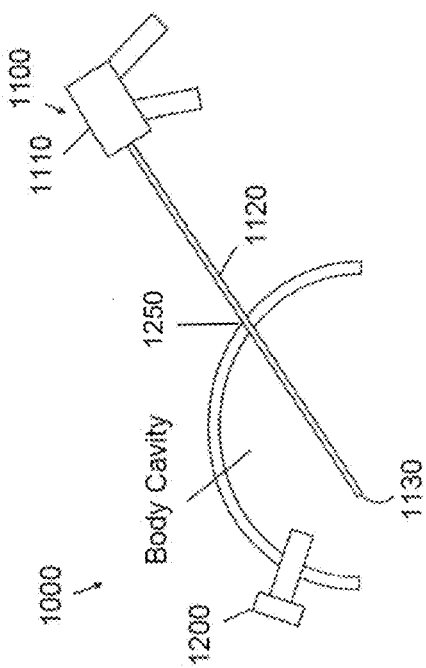
Figure 29D:
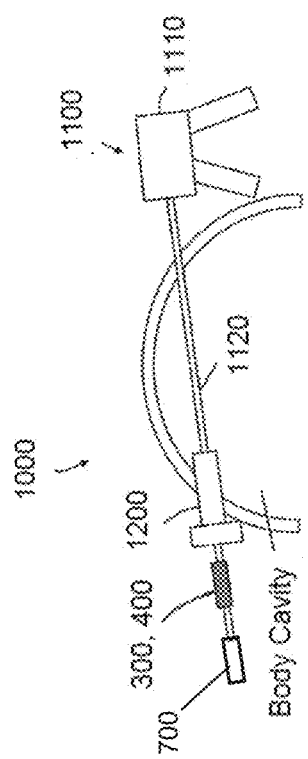

As shown in FIG. 29B, once the distal end of the elongated needle shaft 1120 is extended from the access port 1200 to the external environment, the surgical clip cartridge 300, 400 may be attached to an outer surface of the elongated needle shaft 1120. For example, a snap-on surgical clip cartridge, such as the surgical clip cartridge 300, 400 may be snapped onto the outer surface of the elongated needle shaft 1120, as shown in FIG. 29C. Alternatively, a snap-on clip cartridge, such as the surgical clip cartridge 500 may be secured onto or over the needle tip 1130 of the elongated needle shaft 1120. Once the snap-on clip cartridge has been secured to the elongated needle shaft 1120, the elongated needle shaft 1120 and the snap-on clip cartridge 300, 400 may be withdrawn into the body cavity via the access port 1200, as shown in FIG. 29D. The process may then be reversed, as generally shown in FIGS. 29G and 29H, in order to remove or snap-off the clip cartridge 300, 400 from the elongated needle shaft 1120 such that the surgical tool 1100 can be removed from the patient, via the initial incision or opening 1250, without creating a larger incision.

In addition to attaching or snapping on the surgical clip cartridge 300, 400 onto the outer surface of the elongated needle shaft 1120, as shown generally in FIGS. 29B and 29C, an end effector tool 700 may also be attached to the distal end of the elongated needle shaft 1120. The end effector tool 700 may be one of graspers, scissors, clamp, a cauterizing end, a biopsy probe, a snare loop, a needle knife, a camera and a light source. Of course, other tools and end effectors for the surgical tool 1100 are of course contemplated.

Figure 29E:
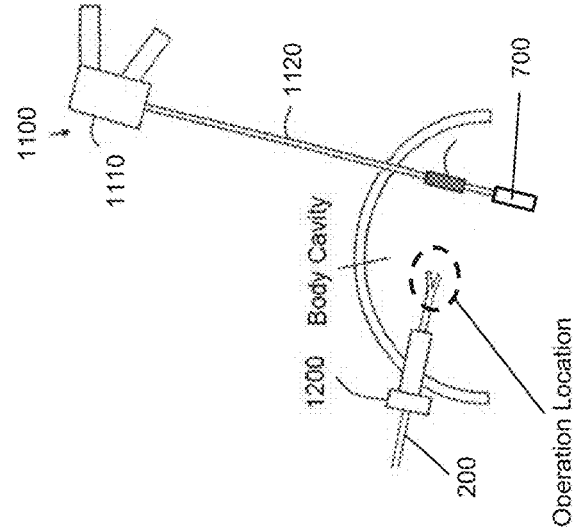

As shown in FIG. 29E, once the surgical clip cartridge 300, 400 mounted onto the elongated shaft 1120 has been withdrawn into the body cavity, a clip applier such as the clip applier 200 (shown and discussed with reference to FIGS. 4A and 4B above) may be used within the body cavity to apply a plurality of surgical clips. In particular, the first jaw 210 and the second jaw 220 of the clip applier 200 may be introduced through the access port 1200 and guided towards the surgical clip cartridge 300, 400 such that surgical clips 100 may be retrieved from the surgical clip cartridge 300, 400 while within the body cavity.

Figure 29F:
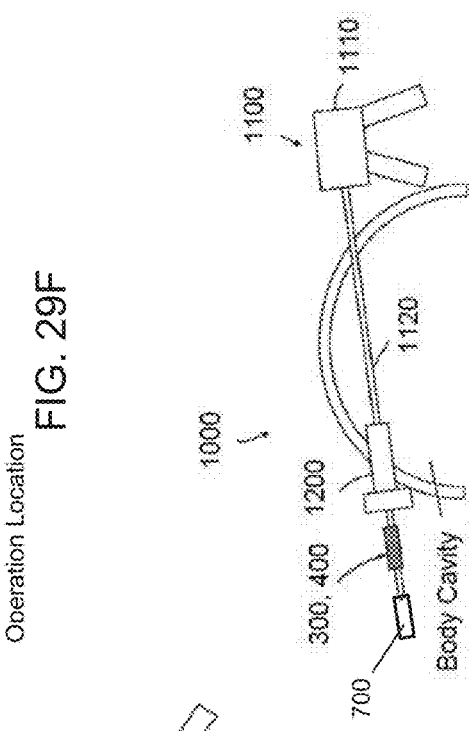
Figure 29G:
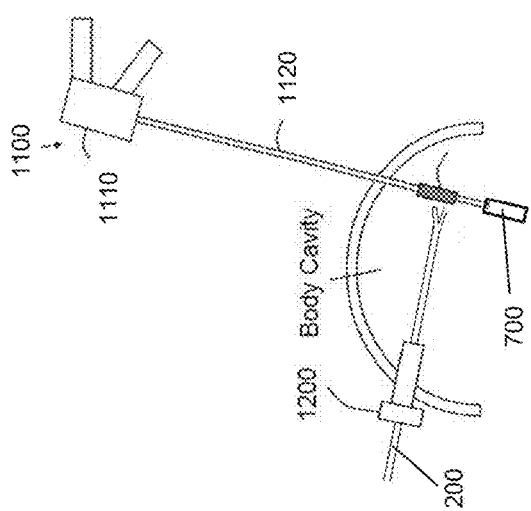
Figure 29H:
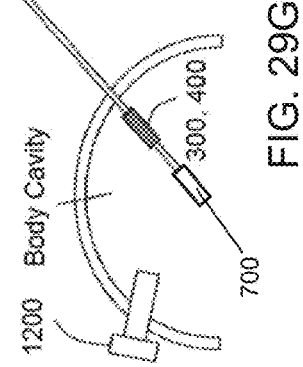

As generally shown in FIGS. 29E and 29F, a first surgical clip may be retrieved using the clip applier 200 from the surgical clip cartridge 300, 400. The first surgical clip may then be applied to clamp at least one portion of a vessel or piece of tissue located in at least one operation location within the body cavity. While remaining within the body cavity, the clip applier 200 may then retrieve a second surgical clip from the surgical clip cartridge 300, 400. The second surgical clip may then be applied to clamp the same or another portion of the vessel or piece of tissue. Alternatively, the second surgical clip may be applied to a different vessel or piece of tissue within the body cavity. Additional surgical clips may be retrieved from the surgical clip cartridge 300, 400 and applied by the clip applier 200 without either the clip applier 200 or the surgical clip cartridge 300, 400 from having to be removed from the body cavity.

By providing the surgical clip cartridge 300, 400 within the body cavity, a shorter travel distance is required between reloading of the clip applier 200, and reloading can be accomplished intracorporeally, thereby providing a more efficient ligation process and reducing contamination or complications that may arise by having a surgeon repeatedly remove and re-insert a clip applier into and out of the body cavity for reloading purposes.

An exemplary surgical method of using the micro-laparoscopic system 1000 will now be described. The surgical method may include a step of providing the surgical clip cartridge 300, 400, the surgical tool 1100 with the elongated needle shaft 1120, and the access port 1200. The surgical clip cartridge may include between four and eight clip slots for transporting a corresponding number of surgical clips. The access port 1200 may be inserted into a first opening of the body cavity wall such that at least a portion of the access port 1200 extends into the body cavity. In one aspect, the first opening may be created as pressure is applied against the body cavity wall via the access port 1200. In one aspect, the first opening may be formed at the umbilicus of the patient. In one aspect, the access port 1200 may define a lumen having an internal diameter of between 3 mm to 30 mm, and the first opening may have a minimum diameter of greater than 3 mm.

The method may comprise a step of inserting the elongated needle shaft 1120 into the body cavity via a second opening, the second opening being remote from the first opening. In one aspect, the needle tip 1130 of the elongated needle shaft 1120 may be used to puncture the body cavity wall to thereby forming the second opening. In one aspect, the maximal outer diameter of the elongated needle shaft is 3 mm or less, and the second opening formed may have a maximal diameter of approximately 3 mm or less.

The method may comprise a step of orienting the needle tip 1130 of the elongated needle shaft 1120 towards a distal opening of the access port 1200 that is extended into the body cavity. The needle tip 1130 and at least a distal portion of the elongated needle shaft 1120 may be guided through the lumen of the access port 1200 and out a proximal opening of the access port 1200. Once at least the distal portion of the elongated needle shaft 1120 passes through the proximal opening of the access port 1200 and is accessible in the external environment outside the body cavity, the surgical clip cartridge 300, 400 may be attached to the outer surface of the elongated needle shaft 1120. The surgical clip cartridges 300, 400 may be secured to the elongated needle shaft 1120 via at the least one docking portion 316*a*, 316*b*, 416*a*, 416*b* using a snap-on or annular fit. The at least one docking portion 316*a*, 316*b*, 416*a*, 416*b* may flex as it is being attached to the elongated needle shaft 1120 and may at least partially surround the elongated needle shaft 1120 once attached. The at least one docking portion 316*a*, 316*b*, 416*a*, 416*b* may be slightly expanded once attached to the elongated needle shaft 1120 and may grip the elongated needle shaft 1120 through the presence of hoop strain or stress.

While the distal end of the elongated needle shaft 1120 remains extended from the proximal end of the access port 1200 and accessible to the external environment outside the body cavity, an end effector tool 700 may be mounted to the distal end of the elongated needle shaft 1120. In one aspect, the end effector tool 700 may be one of graspers, scissors, clamp, a cauterizing end, a biopsy probe, a snare loop, a needle knife, a camera and a light source.

Once the surgical clip cartridge 300, 400 has been attached to the elongated needle shaft 1120, both the surgical clip cartridge 300, 400 and the distal end of the elongated needle shaft 1120 may be withdrawn into the body cavity via the lumen of the access port 1200. A plurality of surgical clips carried by the surgical clip cartridge 300, 400 may then be retrieved from the surgical clip cartridge 300, 400 while it is within the body cavity.

In one aspect, a distal end of the clip applier 200 may be inserted into the body cavity via the access port 1200. The distal end of the clip applier 200 may include a pair of jaws or other grasping mechanism. The pair of jaws or other grasping mechanism may be maneuvered to at least a first slot of the surgical clip cartridge 300, 400. The pair of jaws may then engage and retrieve a first surgical clip retained within the first slot of the surgical clip cartridge 300, 400. The clip applier 200 may then be directed towards an operation location where the first surgical clip is latched and secured around a target vessel or other type of tissue. The pair of jaws or other grasping mechanism may then be maneuvered to a second slot of the surgical clip cartridge 300, 400 such that a second surgical clip may be retrieved from the second slot of the surgical clip cartridge 300, 400. The clip applier 200 may then be directed towards an operation location where the second surgical clip is latched and secured around target vessel or other type of tissue, which may be the same target vessel or tissue secured by the first surgical clip or it may be different target vessel or tissue as required by the procedure. This process may be repeated such that additional surgical clips may be retrieved from the surgical clip cartridge 300, 400 and applied without having to remove the clip applier 200 from within the body cavity. If present, the end effector tool 700 may be used to perform a procedure within the body cavity while the surgical clip cartridge 300, 400 is mounted to the elongated needle shaft 1120.

Once the number of surgical clips held by the surgical clip cartridge 300, 400 have been exhausted, or once the surgical clips are no longer needed for the operation, the clip applier 200 may be withdrawn from the body cavity by passing the distal end of the clip applier 200 back through the lumen of the access port 1200 and out to the external environment. Both the surgical clip cartridge 300, 400 and the distal end of the elongated needle shaft 1120 may also pass through the lumen of the access port 1200 such that at least the surgical clip cartridge 300, 400 is accessible in the external environment. The surgical clip cartridge 300, 400 may then be detached from the elongated needle shaft 1120. If present, the end effector tool 700 may also be removed from the distal end of the elongated needle shaft 1120.

The distal end of the elongated needle shaft 1120 may be withdrawn back into the body cavity via the lumen of the access port 1200. The surgical tool 1100, including distal end of the elongated shaft 1120, may be completely withdrawn from the body cavity by maneuvering the surgical tool 1100 in a proximal direction from the body cavity wall such that the distal end of the elongated shaft 1120 is passes through and exits via the second opening. Although exemplary steps for a surgical method is presented above, variations and modifications to the steps, including rearrangement of the order and sequence, will be appreciated by one skilled in the art in view of the present disclosure.

The surgical clip cartridges described in the present disclosure may be used in a variety of surgical procedure, including intracorporeal feeding of surgical clips, to reduce surgery time and to minimize visualization loss of the surgeon as a result of clip reloading. The methods and systems of the present disclosure, as described above and shown in the drawings, provide surgical clip cartridges with superior properties to provide surgeons with additional flexibility and maneuverability during operation.

While the apparatus and methods of the present disclosure have been shown and described, it will be appreciated that the foregoing description provides examples of the surgical clip cartridge, which may be used with a surgical instrument. However, it is contemplated that other implementations of the disclosure may differ in detail from the foregoing examples. Each aspect of the disclosure may be used individually or in combination with one another, as will be understood by one skilled in the art in view of the present disclosure. All references to the disclosure or examples thereof are intended to reference the particular example being discussed at that point and are not intended to imply any limitation as to the scope of the disclosure more generally. All language of distinction and disparagement with respect to certain features is intended to indicate a lack of preference for those features, but not to exclude such from the scope of the disclosure entirely unless otherwise indicated.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context.

What is claimed is:

1. A surgical clip cartridge containing a surgical clip, comprising:
   the surgical clip;
   a base portion extending in a longitudinal direction, the base portion having a bottom surface; and
   a plurality of dividers extending from the base portion in a direction opposite of the bottom surface,
   wherein the base portion defines a mounting groove for attaching the base portion onto a surgical instrument shaft,
   wherein the mounting groove defines at least two docking portions, a first docking portion of the at least two docking portions being defined on a proximal end of the base portion in the longitudinal direction, and second docking portion of the at least two docking portions being defined on a distal end of the base portion in the longitudinal direction, and
   wherein the first docking portion and the second docking portion both extend along a common longitudinal axis, each of the first and second docking portions defines a concave surface configured to snap on to and engage the surgical instrument shaft, and the concave surfaces extend between about 180° and about 270° around the longitudinal axis of the first and second docking portions.

2. The surgical clip cartridge of claim 1, wherein the mounting groove extends in a direction parallel to the longitudinal direction.

3. The surgical clip cartridge of claim 1, wherein each of the at least two docking portions define a concave surface configured to snap on to and engage the surgical instrument shaft.

4. The surgical clip cartridge of claim 3, wherein the concave surface has a first radius, and the first radius is less than or equal to an outer radius of the surgical instrument shaft to provide an annular fit when the at least two docking portions are attached to the surgical instrument shaft.

5. The surgical clip cartridge of claim 3, wherein a surface of at least one the first and second docking portions includes one or more of a friction material, knurling, notches, and protrusions to prevent axial or rotational displacement when the at least one of the first and second docking portions is attached to the surgical instrument shaft.

6. The surgical clip cartridge of claim 3, wherein the at least two docking portions extend continuously from a proximal end to a distal end of the base portion.

7. The surgical clip cartridge of claim 6, wherein at least one divider of the plurality of dividers includes at least one wall surface extending away from the base portion in a vertical direction perpendicular to the longitudinal direction.

8. The surgical clip cartridge of claim 7, wherein the at least one wall surface is a planar wall surface.

9. The surgical clip cartridge of claim 7, wherein the at least one divider of the plurality of dividers includes an upper surface, and the upper surface includes at least a horizontally extending segment and a sloped segment extending upwardly towards the horizontally extending segment and towards a center of the at least one divider.

10. The surgical clip cartridge of claim 7, wherein an upper portion of the at least one wall surface includes a latching protrusion, the latching protrusion extending at least in the longitudinal direction.

11. The surgical clip cartridge of claim 10, wherein the latching protrusion is for interfacing with at least one portion of a surgical clip, the at least one portion being one of a surface, a depression, and an orifice of the surgical clip.

12. The surgical clip cartridge of claim 10, wherein the latching protrusion is configured to prevent movement of a surgical clip in directions perpendicular to the longitudinal direction of the base portion.

13. The surgical clip cartridge of claim 6, further comprising a plurality of spacer portions extending from the base portion in the direction opposite of the bottom surface, wherein a spacer portion of the plurality of spacer portions is disposed between pairs of facing dividers of the plurality of dividers.

14. The surgical clip cartridge of claim 13, wherein the spacer portion defines a top surface, the top surface having a concave segment and a convex segment.

15. The surgical clip cartridge of claim 13, wherein the spacer portion defines at least one inwardly tapering section and a depth of the inwardly tapering section increases moving from an upper portion of the spacer portion towards a lower portion of the spacer portion.

16. The surgical clip cartridge of claim 1, further comprising a tapering rib extending from one of the first docking portion and the second docking portion, the tapering rib defining a convex or curvilinear tapering profile narrowing towards a longitudinal end of the surgical clip cartridge.

17. A surgical device, comprising:
a surgical instrument with an elongated shaft extending along a first longitudinal axis;
a surgical clip; and
a surgical clip cartridge containing the surgical clip, the surgical clip cartridge including a base portion extending along a second longitudinal direction, the base portion defining a mounting groove to secure the surgical clip cartridge onto at least a portion of the elongated shaft of the surgical instrument,
wherein the mounting groove includes at least one docking portion, the at least one docking portion defining a concave surface configured to snap on to and engage the elongated shaft, and the concave surface extends between about 180° and about 270° around the second longitudinal axis.

18. The surgical device of claim 17, wherein the surgical clip cartridge includes a plurality of dividers extending from the base portion in a direction opposite of a bottom surface of the base portion, and wherein pairs of facing dividers of the plurality of dividers are configured to receive and retain a surgical clip of the surgical clips therebetween.

* * * * *